United States Patent [19]
Larsen et al.

[11] Patent Number: 5,873,886
[45] Date of Patent: Feb. 23, 1999

[54] SURGICAL CUTTING APPARATUS

[75] Inventors: Scott W. Larsen, Newtown; Oleg Shikhman, Bridgeport; Christopher McDonnell, Newtown, all of Conn.

[73] Assignee: United States Surgical Corporation, Norwalk, Conn.

[21] Appl. No.: 802,890

[22] Filed: Feb. 18, 1997

Related U.S. Application Data

[63] Continuation of Ser. No. 416,268, Apr. 4, 1995, abandoned.

[51] Int. Cl.$^6$ .................................................. A61B 17/32
[52] U.S. Cl. ...................... 606/180; 606/170; 606/172; 606/167; 606/159
[58] Field of Search ................................. 606/170, 171, 606/180, 172, 173, 167, 159

[56] References Cited

U.S. PATENT DOCUMENTS

| | | | |
|---|---|---|---|
| Re. 33,258 | 7/1990 | Onik et al. ............................... | 606/171 |
| 3,606,878 | 9/1971 | Kellogg, Jr. . | |
| 4,099,529 | 7/1978 | Peyman .................................. | 606/171 |
| 4,111,207 | 9/1978 | Seiler, Jr. ............................... | 606/171 |
| 4,201,213 | 5/1980 | Townsend .............................. | 606/174 |
| 4,246,902 | 1/1981 | Martinez ................................. | 604/22 |
| 4,282,884 | 8/1981 | Boebel ................................... | 128/751 |
| 4,369,788 | 1/1983 | Goald . | |
| 4,461,305 | 7/1984 | Cibley ................................... | 606/180 |
| 4,530,356 | 7/1985 | Helfgott et al. ........................ | 606/171 |
| 4,589,414 | 5/1986 | Yoshida et al. ........................ | 604/22 |
| 4,603,694 | 8/1986 | Wheeler ................................ | 604/22 |
| 4,620,547 | 11/1986 | Boebel ................................... | 128/754 |
| 4,651,753 | 3/1987 | Lifton ..................................... | 128/751 |
| 4,674,501 | 6/1987 | Greenberg . | |
| 4,722,338 | 2/1988 | Wright et al. ........................... | 606/83 |
| 4,733,663 | 3/1988 | Farley .................................... | 606/83 |
| 4,777,948 | 10/1988 | Wright ................................... | 606/83 |
| 4,850,354 | 7/1989 | McGurk-Burleson et al. ......... | 604/22 |
| 4,955,887 | 9/1990 | Zirm ...................................... | 606/170 |
| 4,961,430 | 10/1990 | Sheahon ................................ | 606/171 |
| 4,976,269 | 12/1990 | Mehl . | |
| 4,990,148 | 2/1991 | Worrick, III et al. .................. | 606/170 |
| 4,994,024 | 2/1991 | Falk ....................................... | 606/83 |
| 5,007,917 | 4/1991 | Evans ..................................... | 606/170 |
| 5,026,375 | 6/1991 | Linovitz et al. ........................ | 606/79 |
| 5,031,634 | 7/1991 | Simon .................................... | 128/754 |
| 5,106,364 | 4/1992 | Hayafuji et al. ....................... | 606/171 |
| 5,174,300 | 12/1992 | Bales et al. ............................ | 606/170 |
| 5,176,628 | 1/1993 | Charles et al. ......................... | 606/171 |
| 5,176,699 | 1/1993 | Markham ............................... | 606/206 |
| 5,226,910 | 7/1993 | Kajiyama et al. ...................... | 606/171 |
| 5,250,059 | 10/1993 | Andreas et al. ........................ | 606/170 |
| 5,250,065 | 10/1993 | Clement et al. ........................ | 606/172 |

(List continued on next page.)

FOREIGN PATENT DOCUMENTS

| | | |
|---|---|---|
| 0 235 489 | 9/1987 | European Pat. Off. . |
| 2808911 | 3/1979 | Germany . |
| 85 18 482.9 | 9/1985 | Germany . |
| 9307621 | 7/1993 | Germany . |
| 4341734 | 9/1994 | Germany . |
| 2022421 | 12/1979 | United Kingdom . |
| 9505123 | 2/1995 | WIPO . |

OTHER PUBLICATIONS

Rough translating of paragraphs bridging pp. 11 and 12 of the text is provided.

Primary Examiner—Michael Powell Buiz
Assistant Examiner—Daphna Shai

[57] ABSTRACT

A surgical apparatus for cutting and storing sections of body tissue is provided comprising a housing having a handle assembly, an elongated outer tube extending from the handle assembly, and a cutting tube positioned within the outer tube and movable in response to actuation of the handle assembly between a retracted position and a distal position to cut body tissue. The cutting tube has a chamber formed therein for storing the cut tissue sections. An anvil is positioned at a distal end of the outer tube for forcing each cut tissue section proximally into the chamber of the cutting tube as the cutting tube is advanced to cut the body tissue.

21 Claims, 21 Drawing Sheets

U.S. PATENT DOCUMENTS

| | | | |
|---|---|---|---|
| 5,269,797 | 12/1993 | Bonati et al. | 606/170 |
| 5,269,798 | 12/1993 | Winkler | 606/170 |
| 5,273,519 | 12/1993 | Koros et al. | 606/170 |
| 5,286,255 | 2/1994 | Weber | 606/170 |
| 5,290,303 | 3/1994 | Pingleton et al. | 606/170 |
| 5,308,358 | 5/1994 | Bond et al. | 606/205 |
| 5,314,424 | 5/1994 | Nicholas . | |
| 5,316,013 | 5/1994 | Striebel, II et al. . | |
| 5,320,110 | 6/1994 | Wang | 128/753 |
| 5,324,301 | 6/1994 | Drucker | 606/170 |
| 5,327,896 | 7/1994 | Schmieding | 128/753 |
| 5,330,502 | 7/1994 | Hassler et al. | 606/170 |
| 5,336,238 | 8/1994 | Holmes et al. | 606/208 |
| 5,374,277 | 12/1994 | Hassler . | |
| 5,375,608 | 12/1994 | Tiefenbrun et al. | 128/754 |
| 5,385,570 | 1/1995 | Chin et al. | 606/170 |
| 5,423,844 | 6/1995 | Miller | 606/171 |
| 5,439,474 | 8/1995 | Li | 606/184 |
| 5,451,227 | 9/1995 | Michaelson | 606/170 |
| 5,476,473 | 12/1995 | Heckele . | |
| 5,496,347 | 3/1996 | Hashiguchi et al. . | |
| 5,507,774 | 4/1996 | Holmes et al. . | |

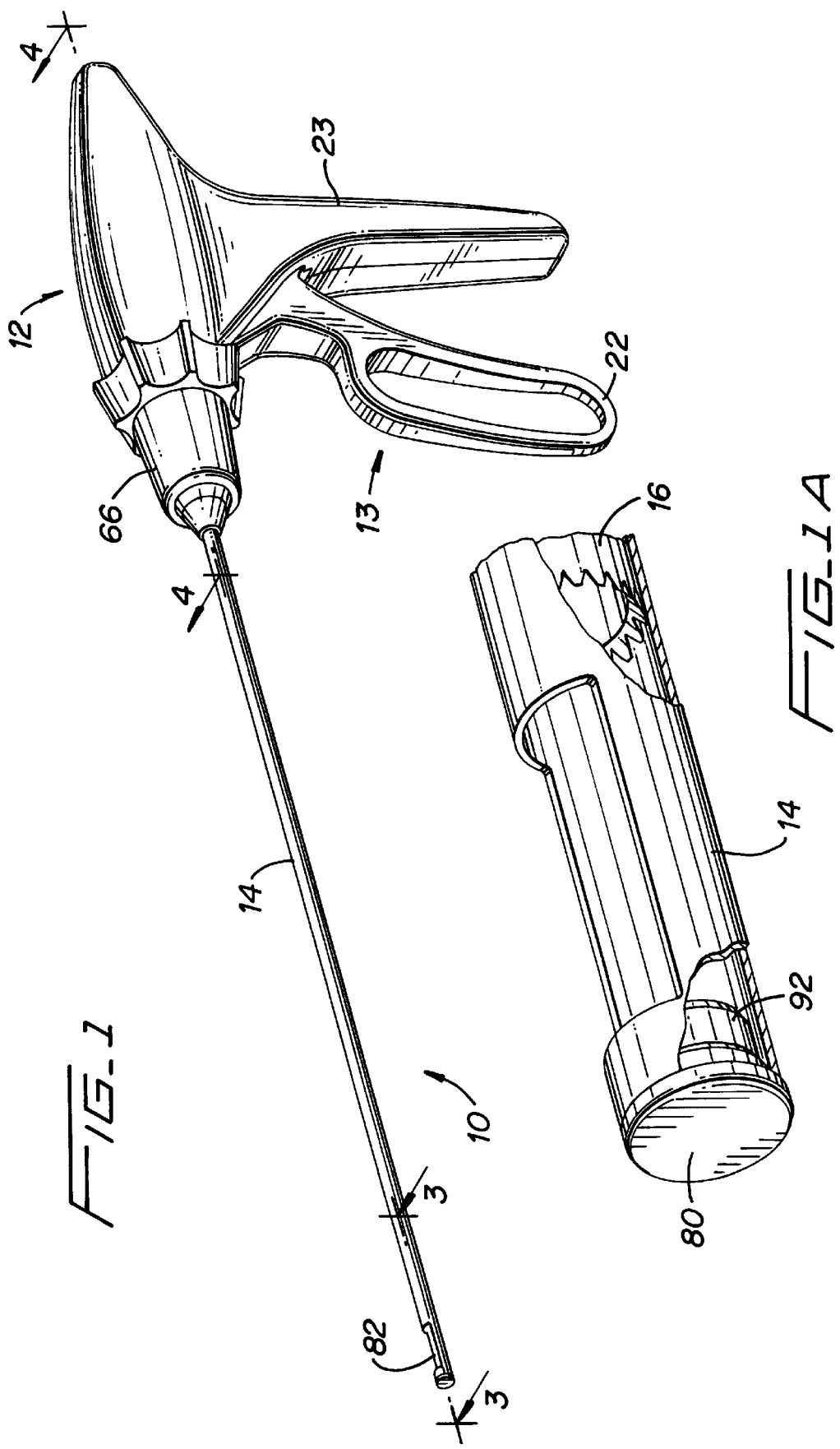

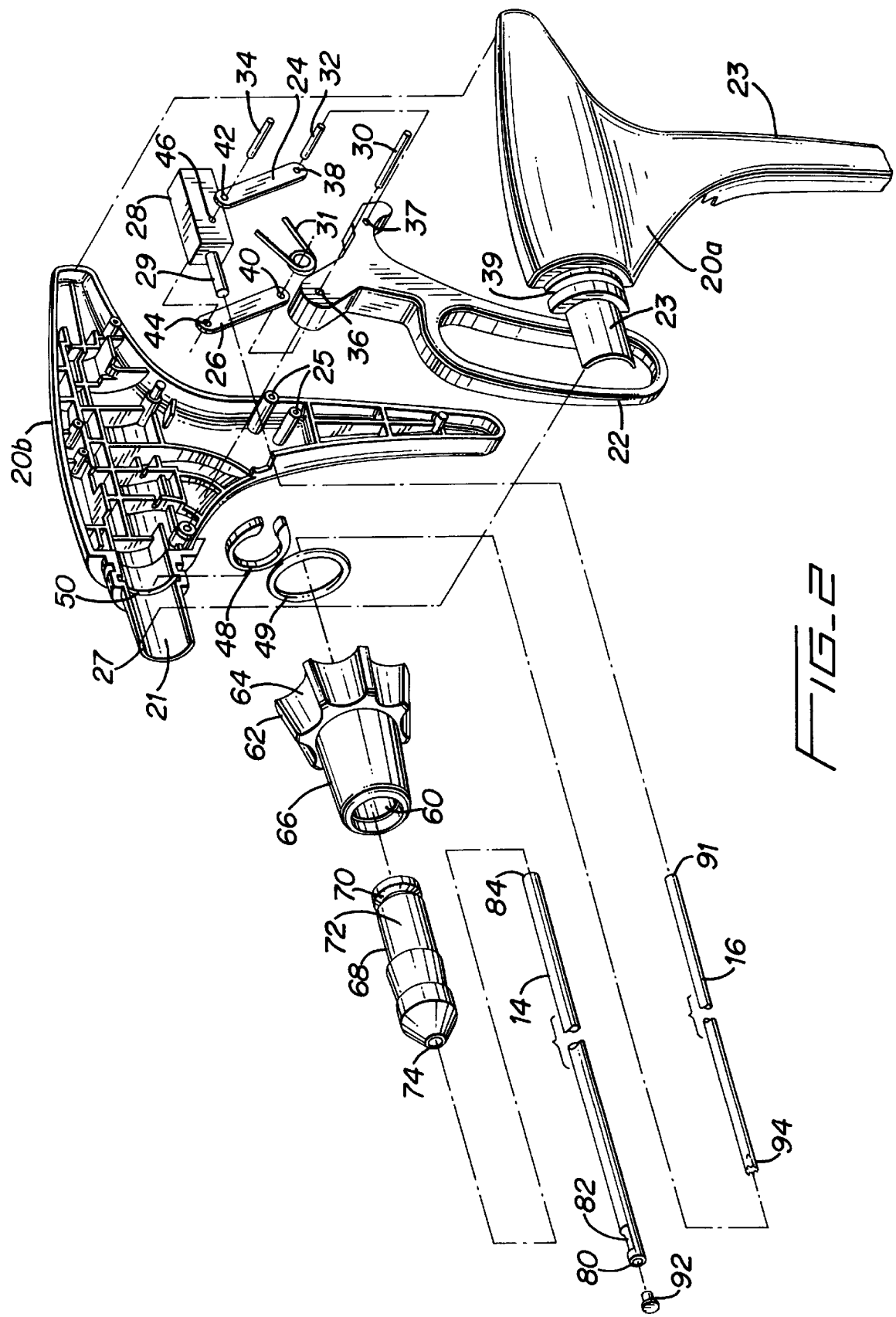

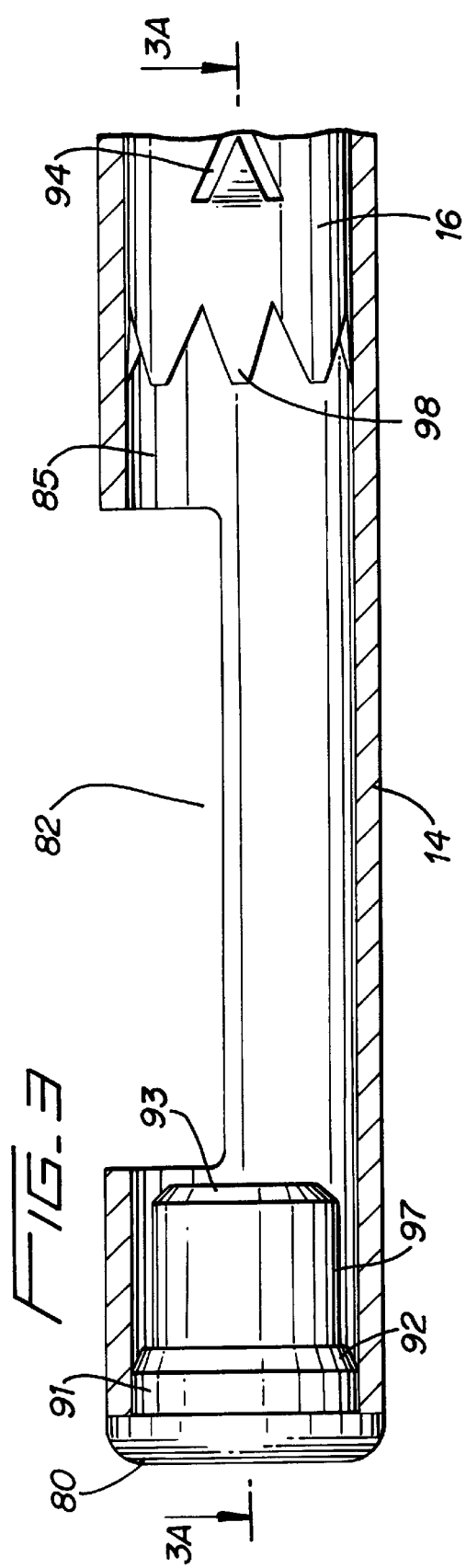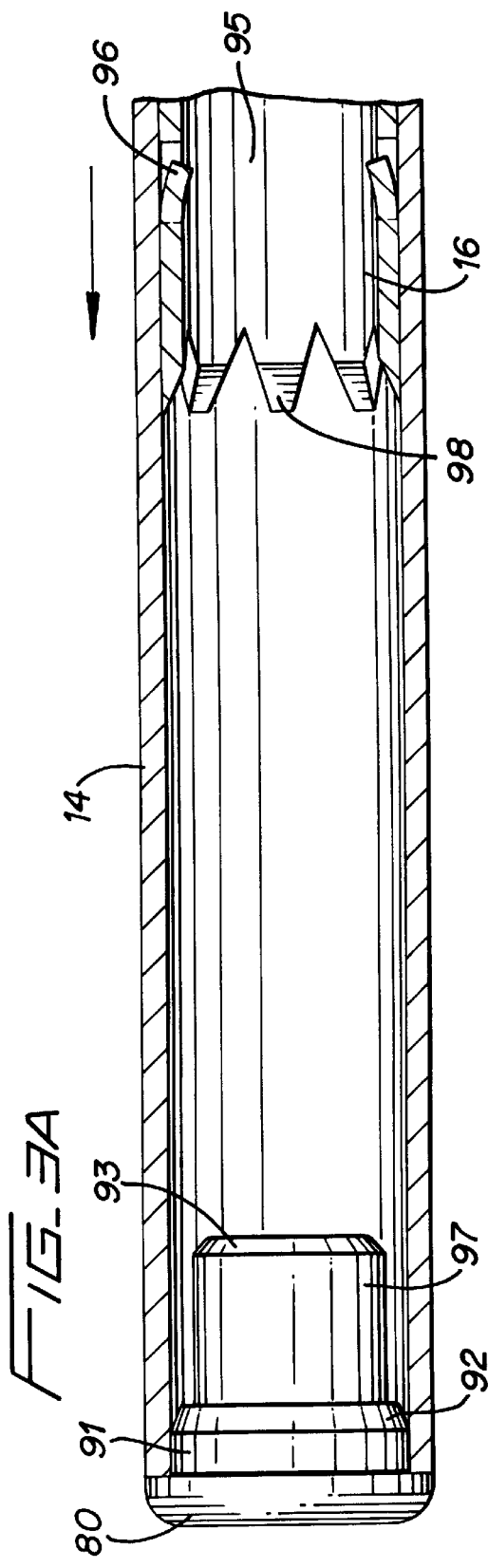

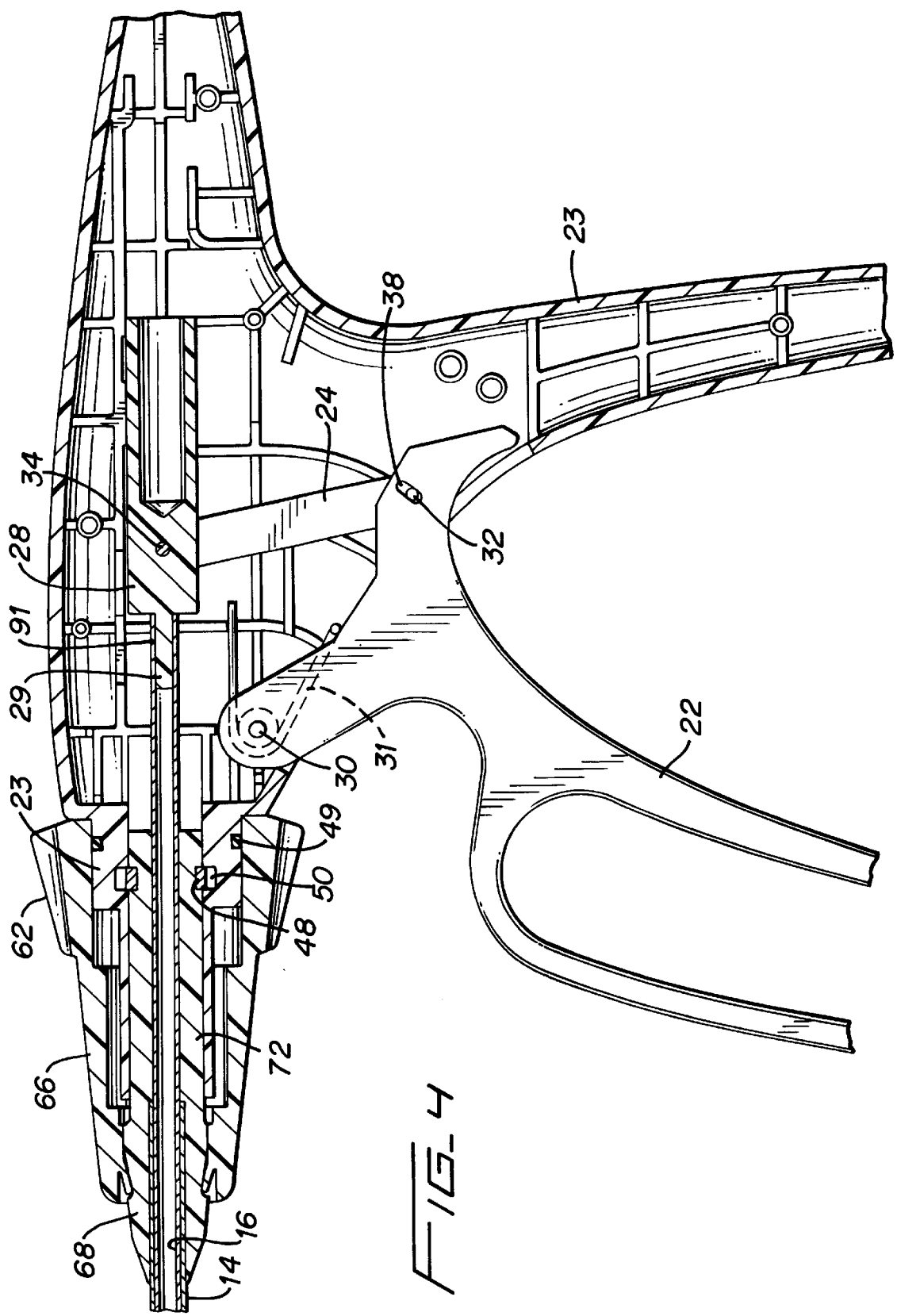

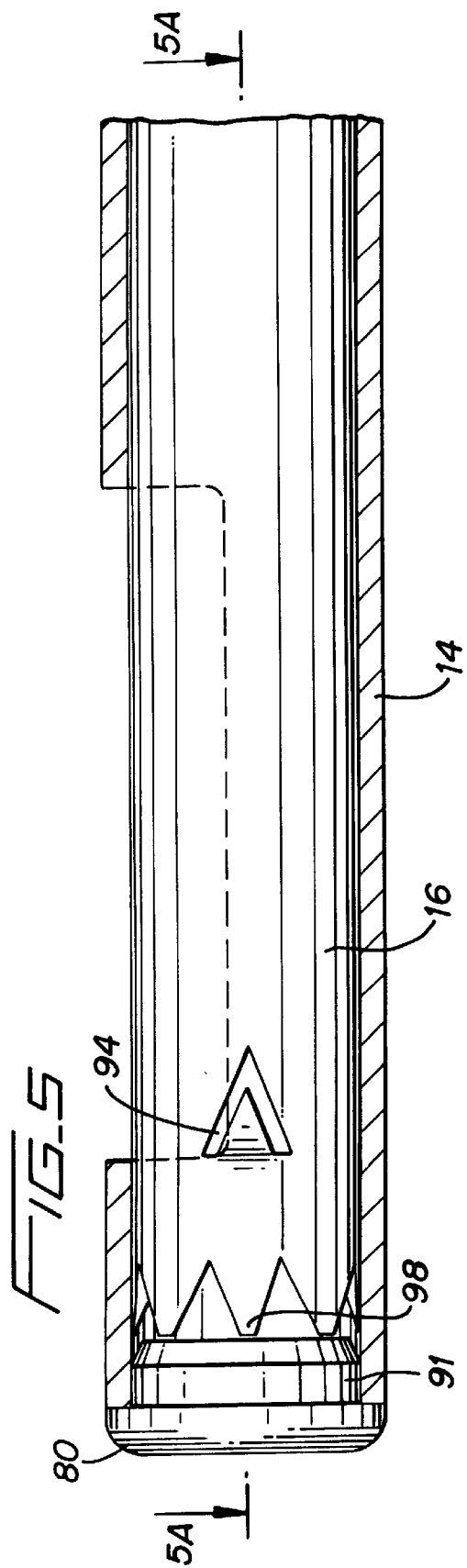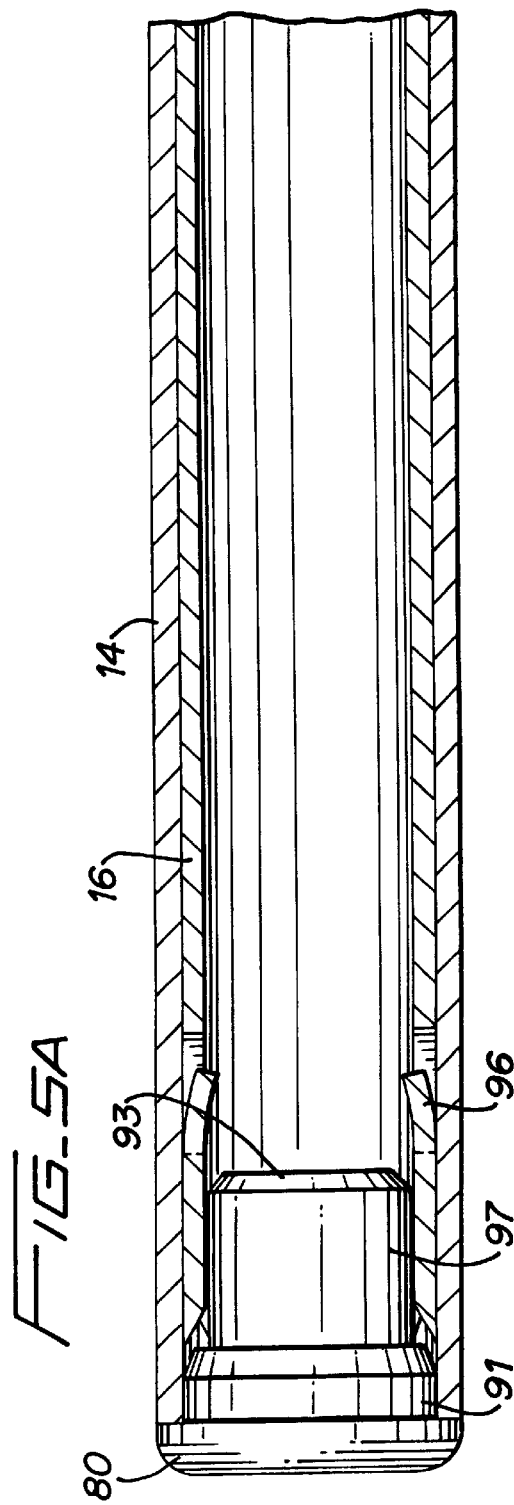

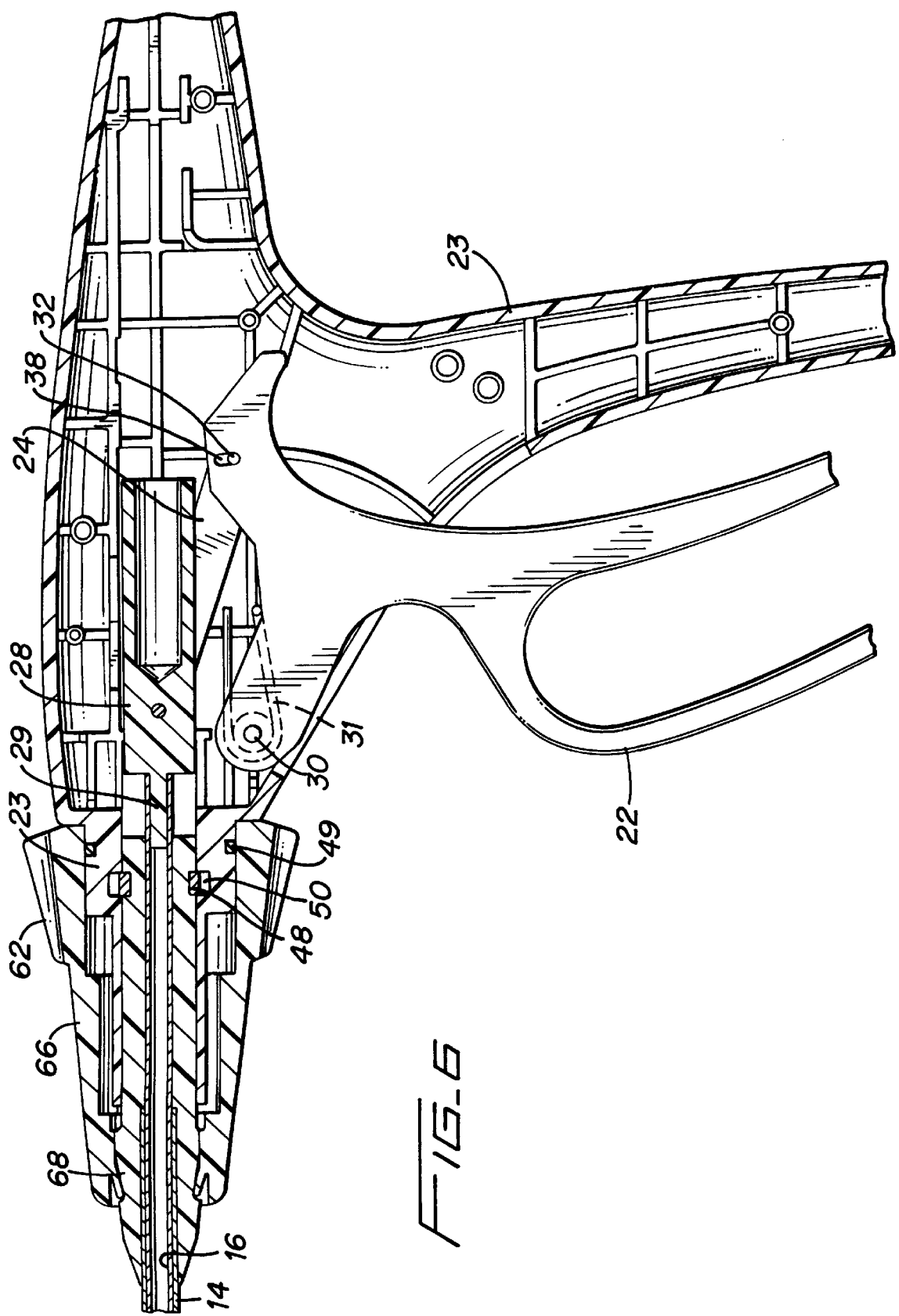

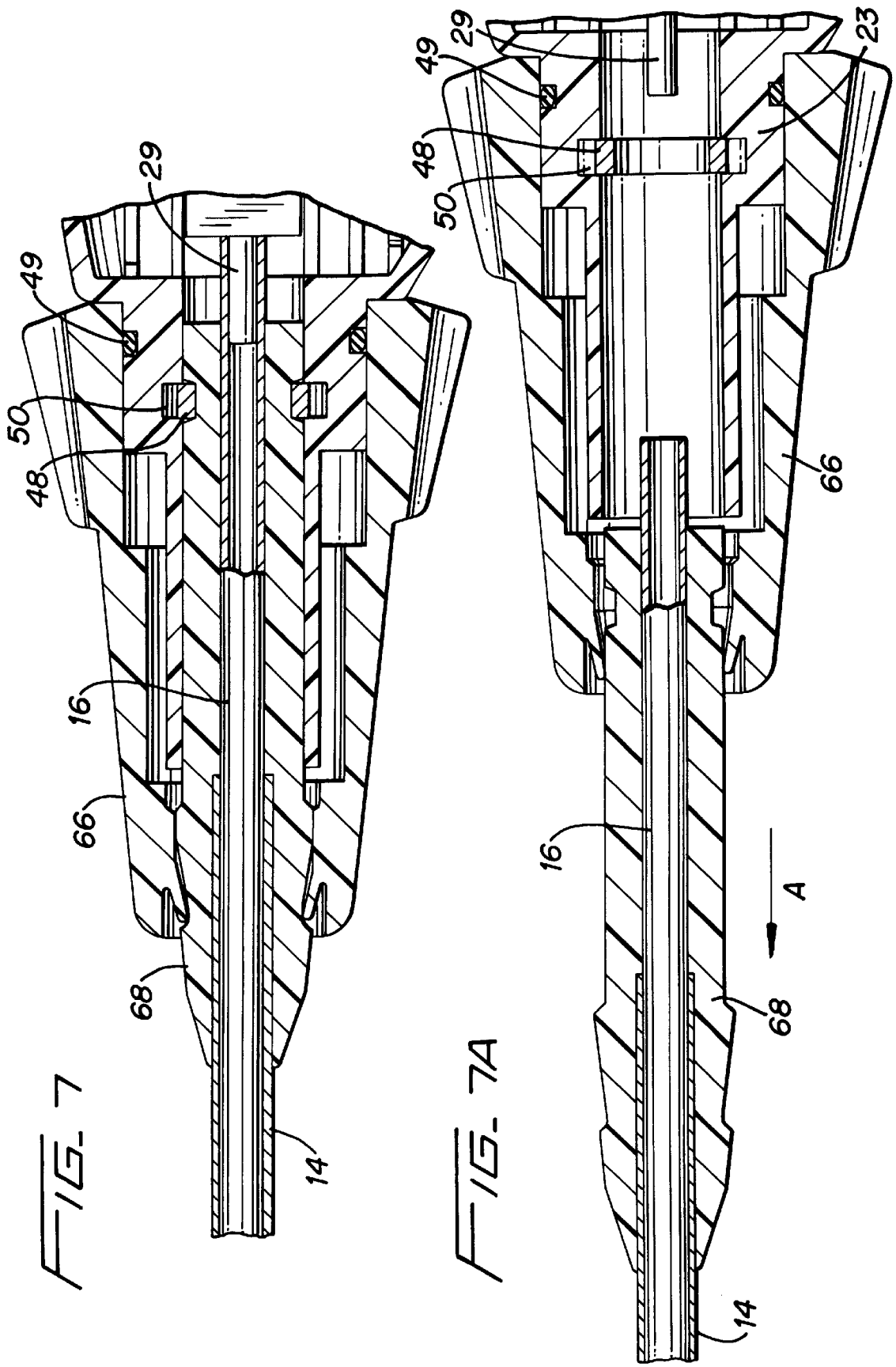

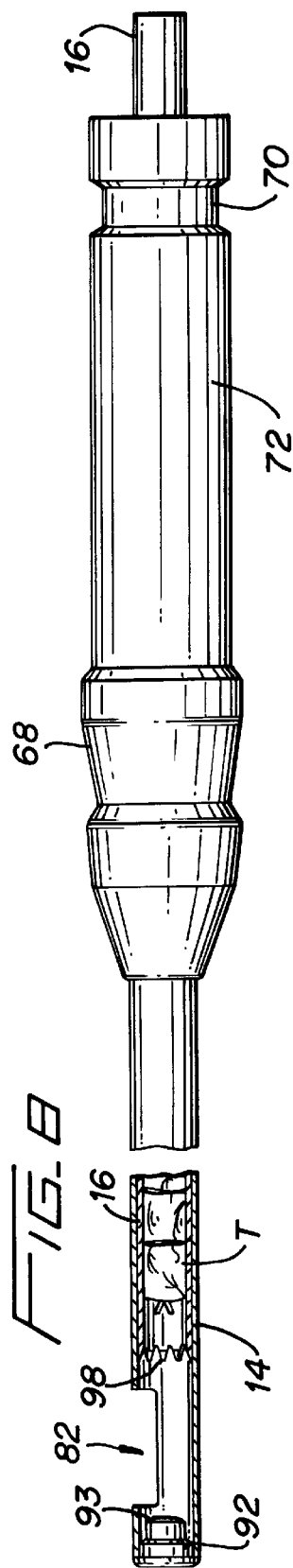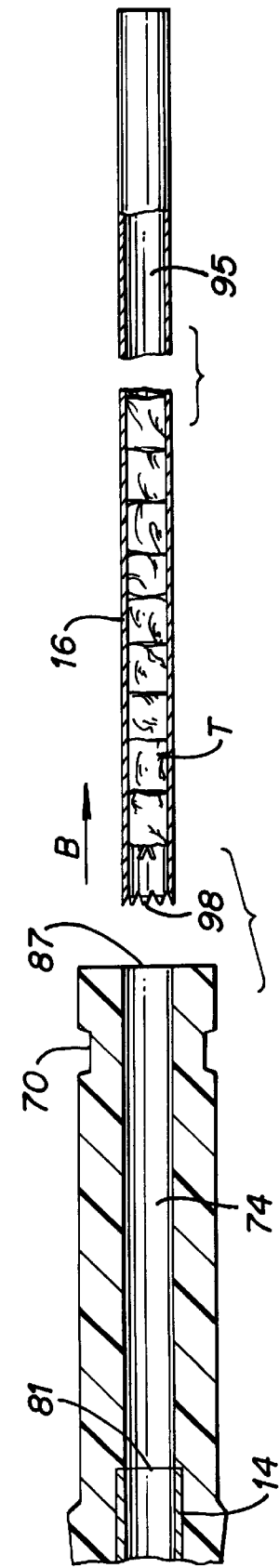

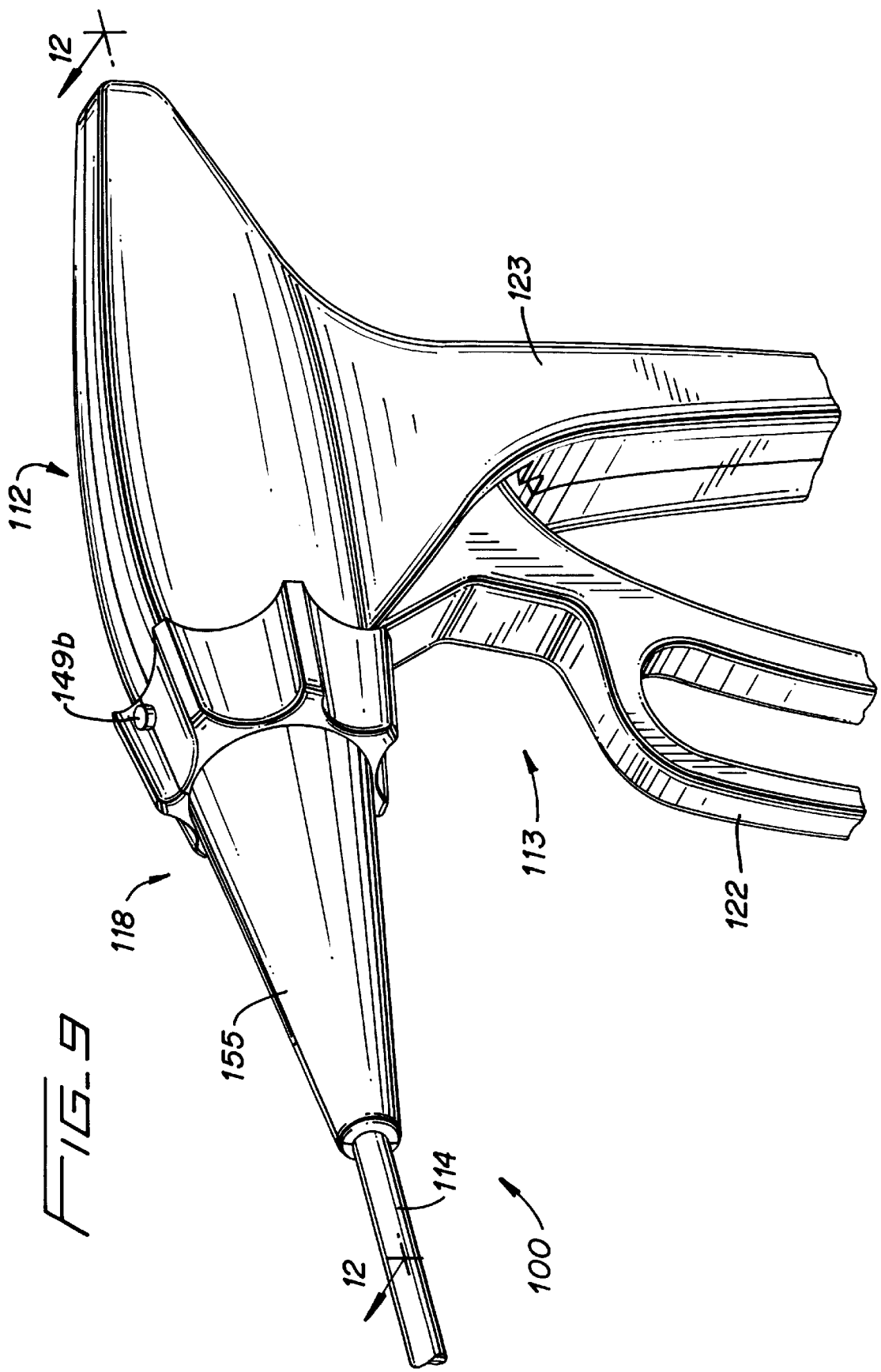

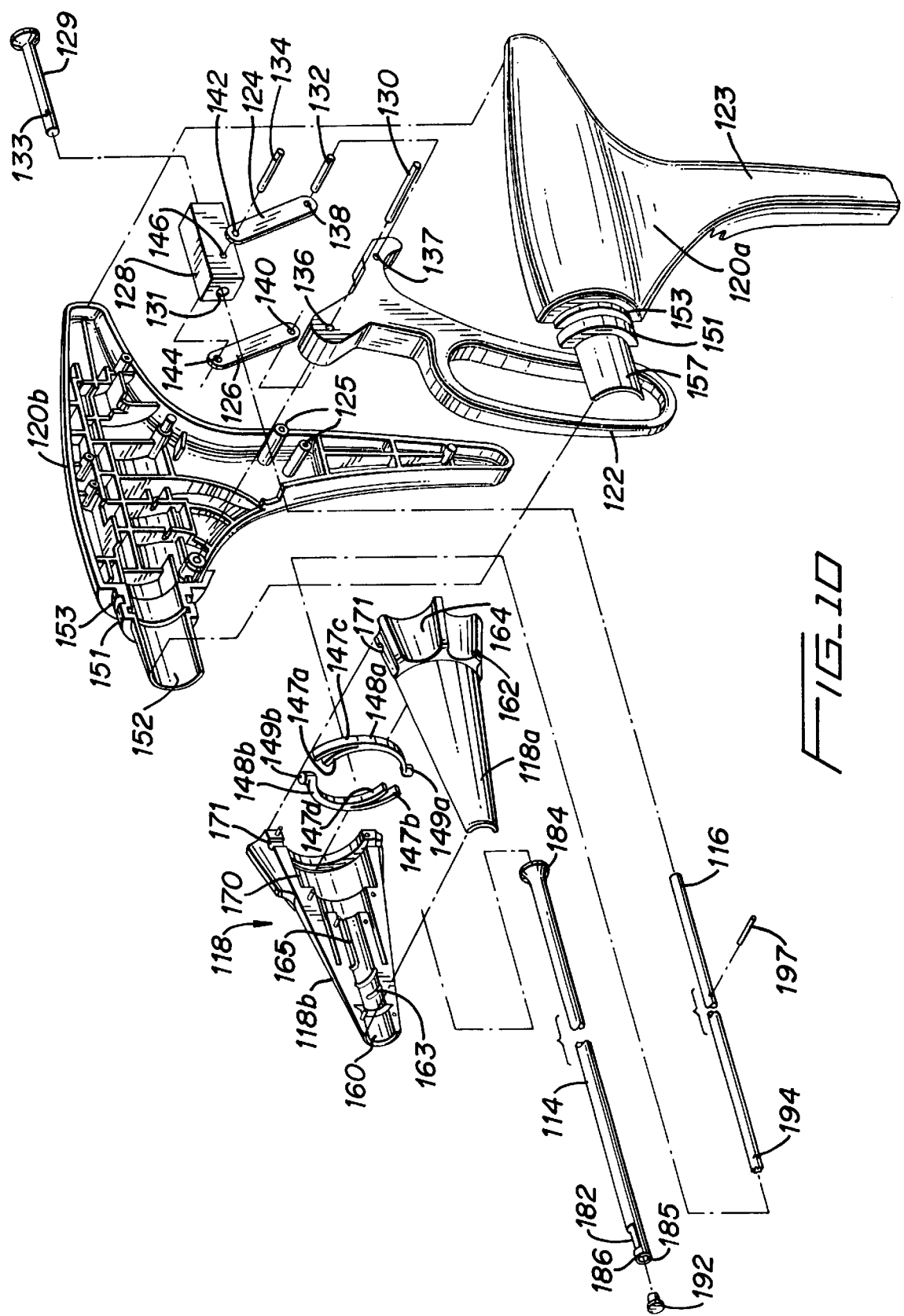

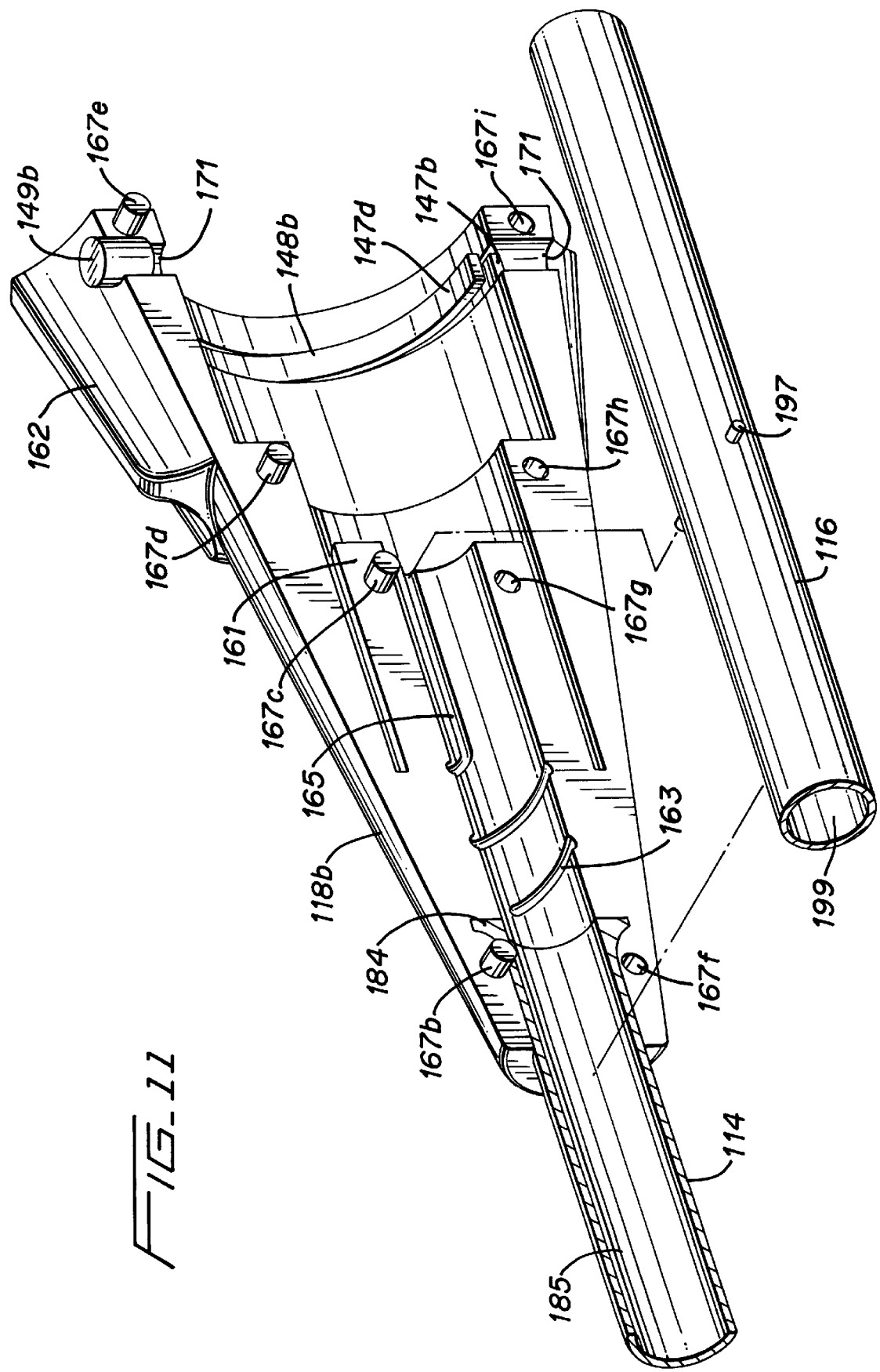

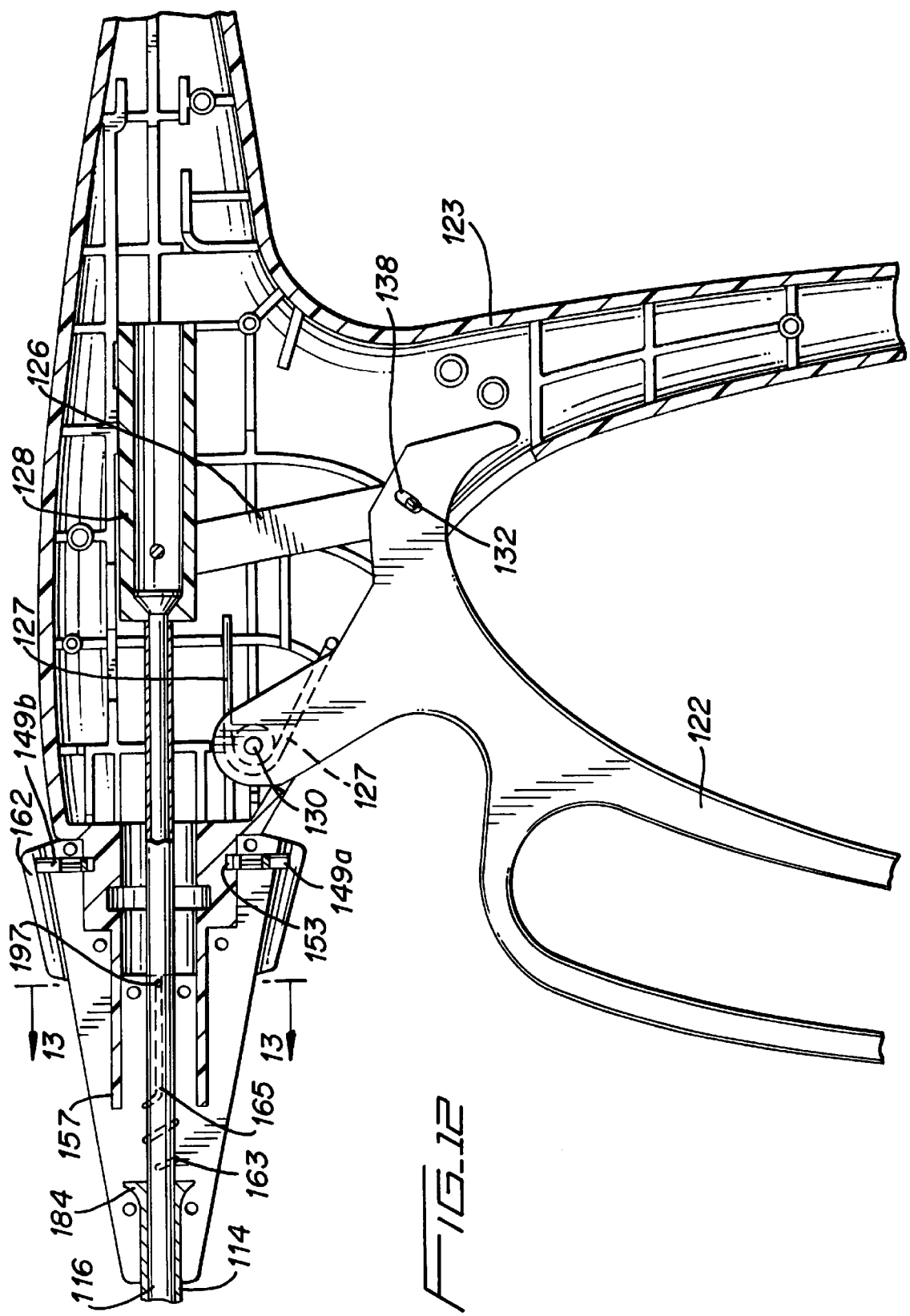

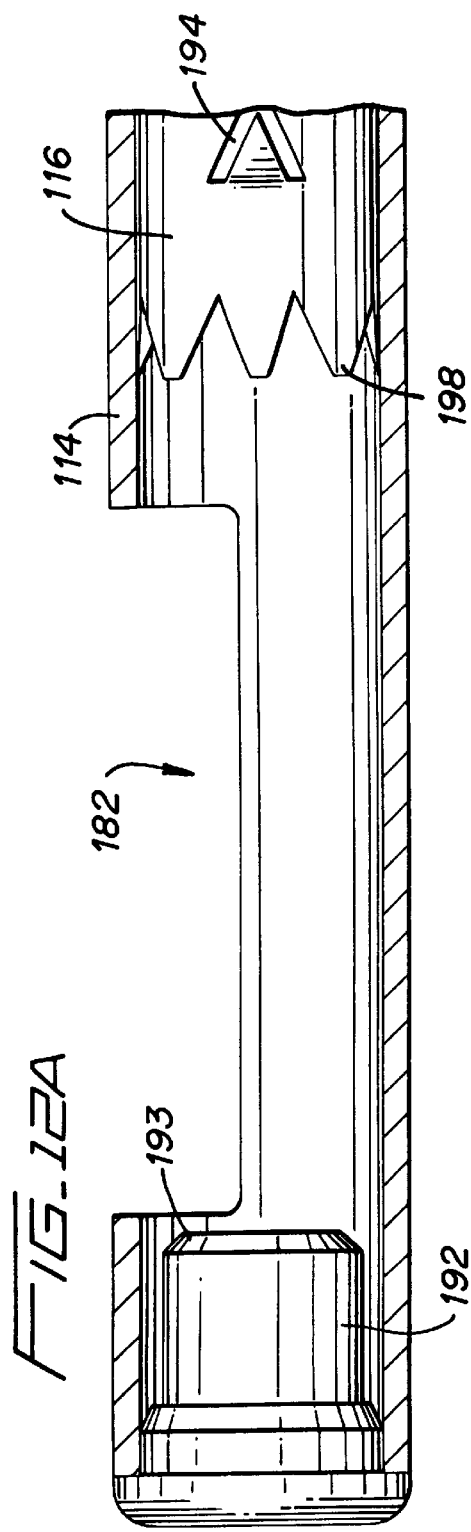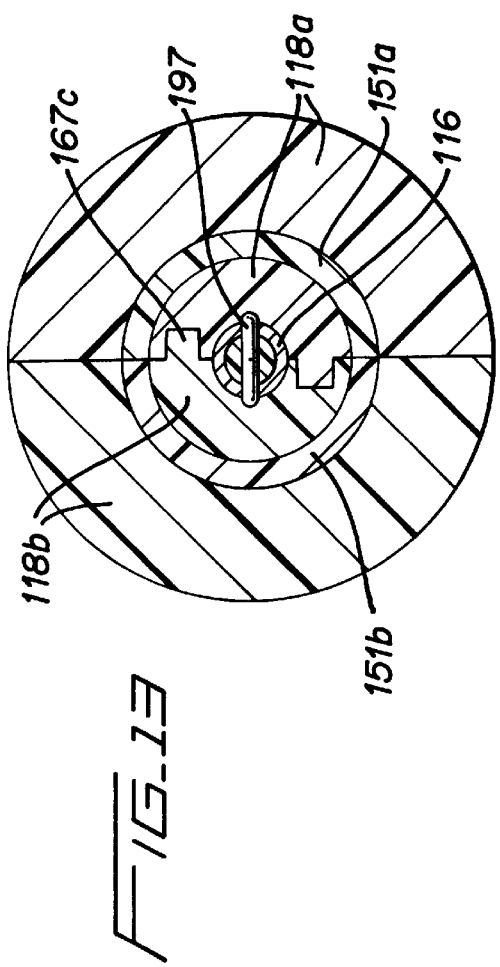

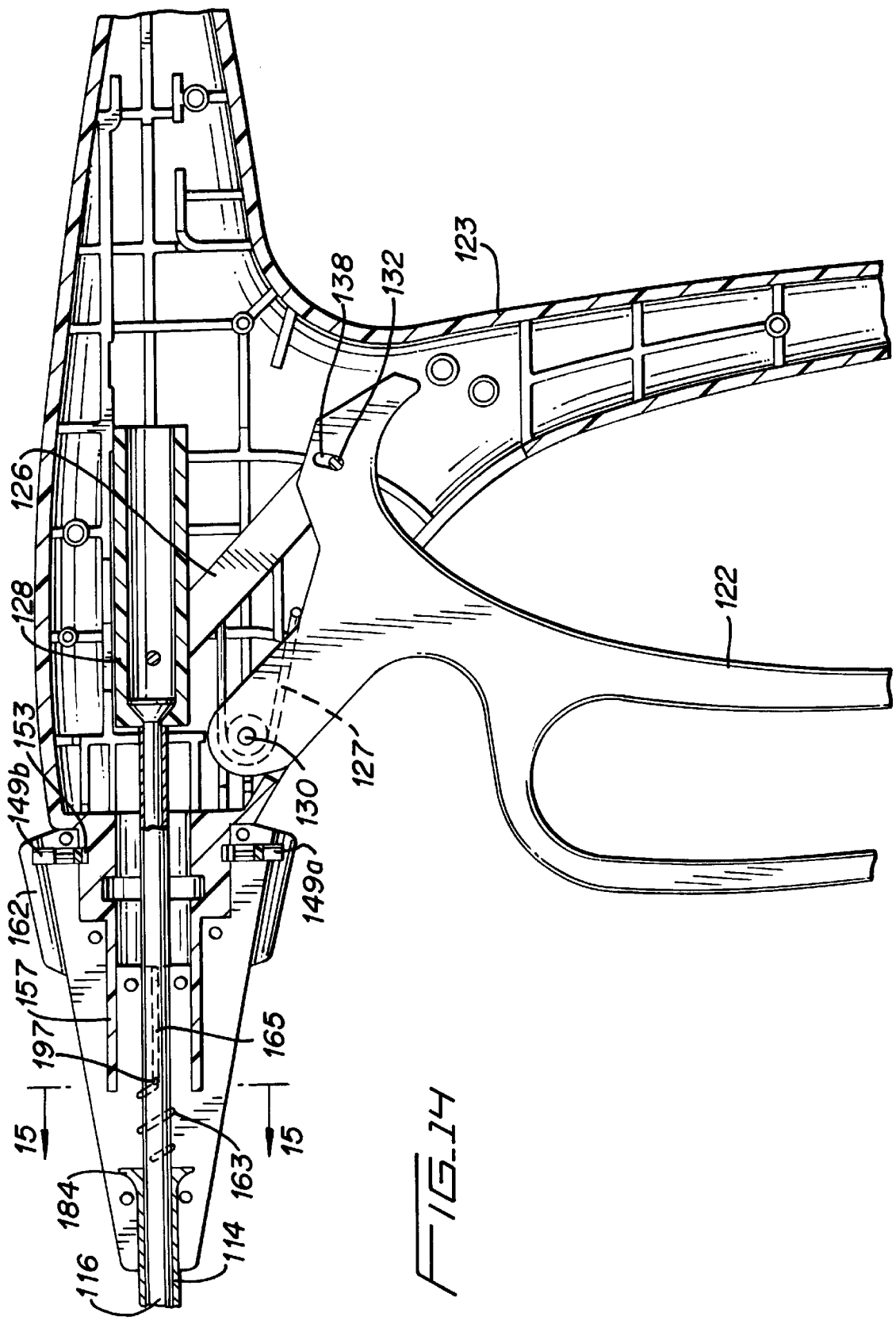

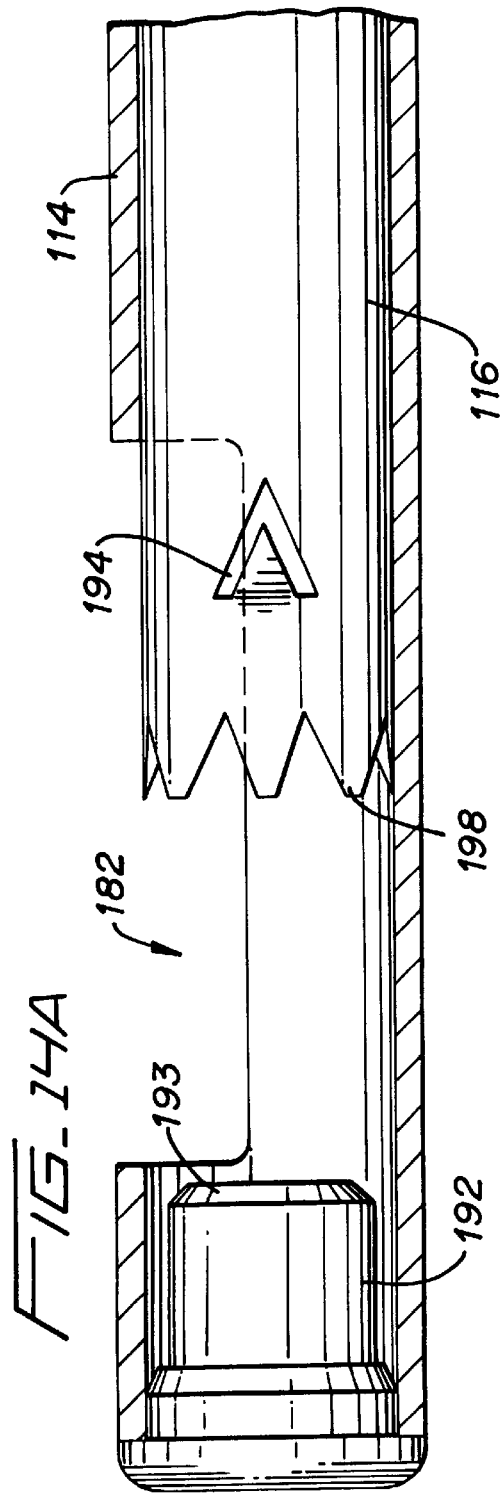
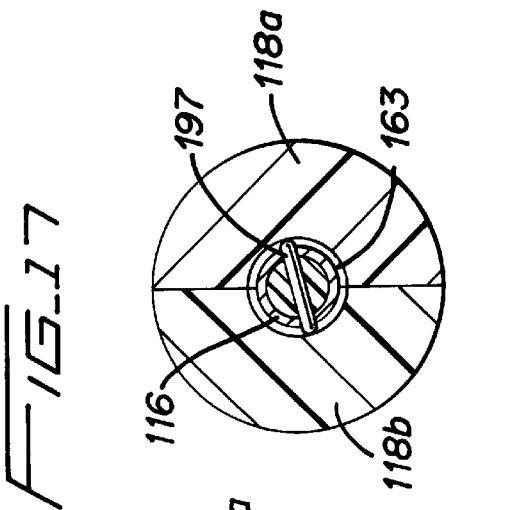
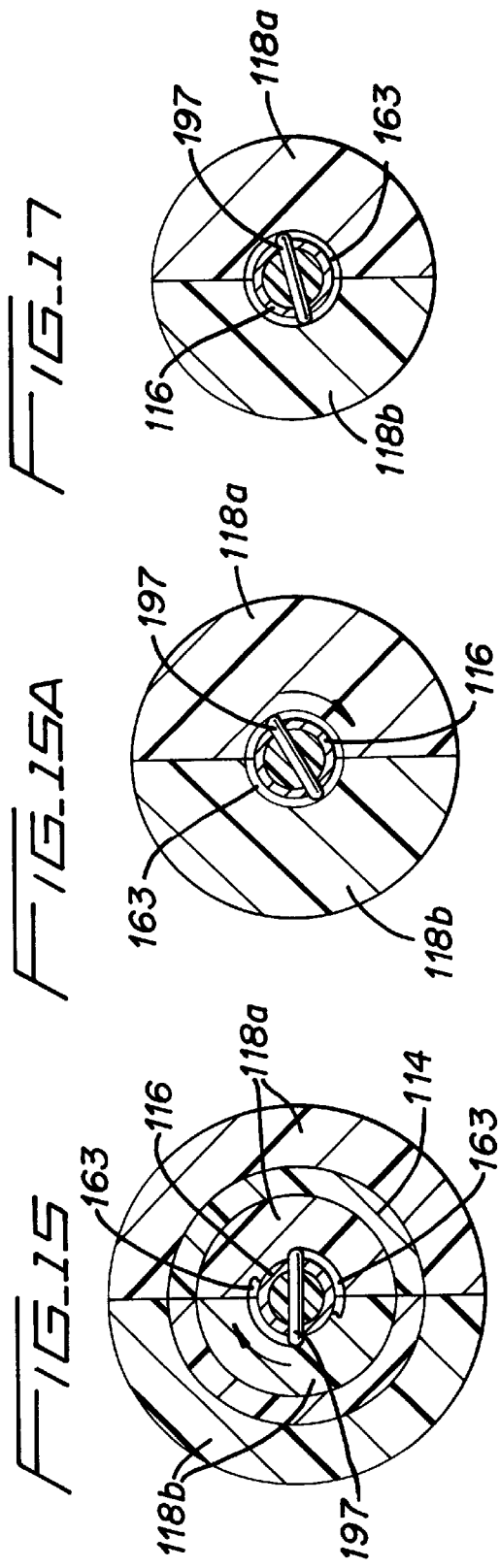

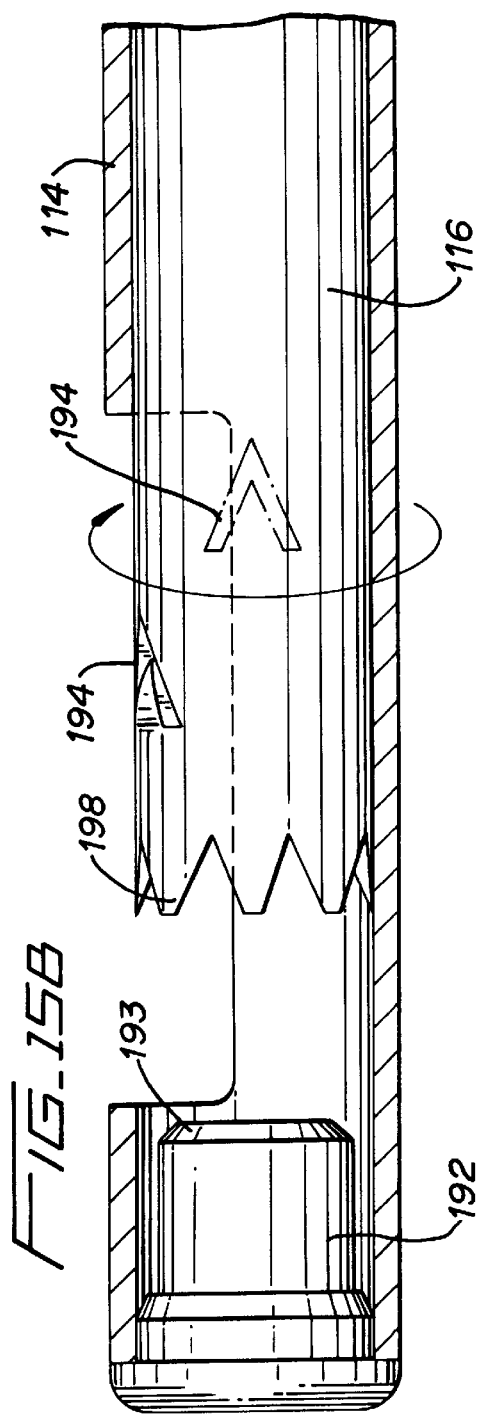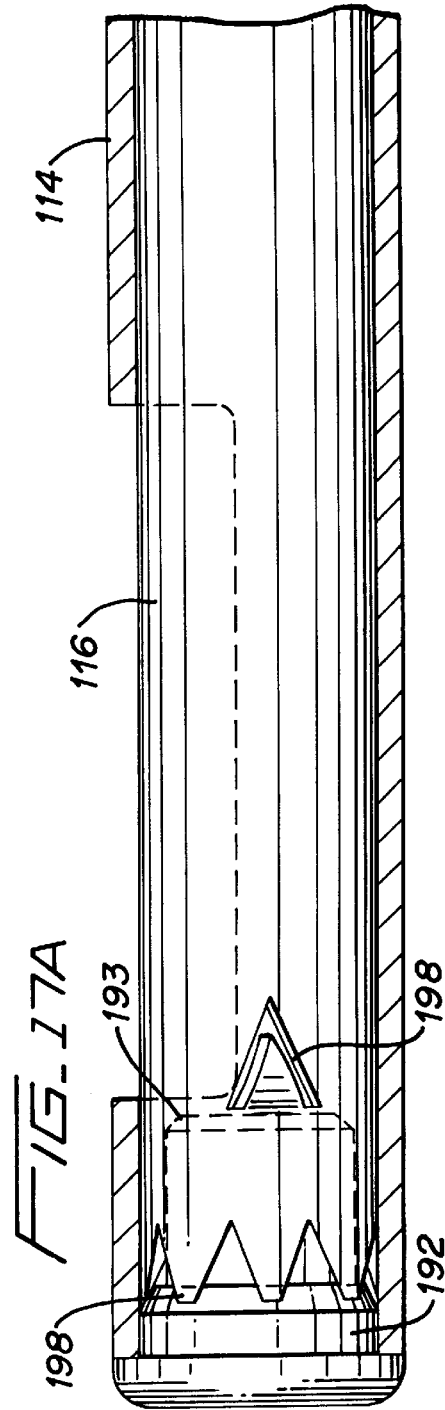

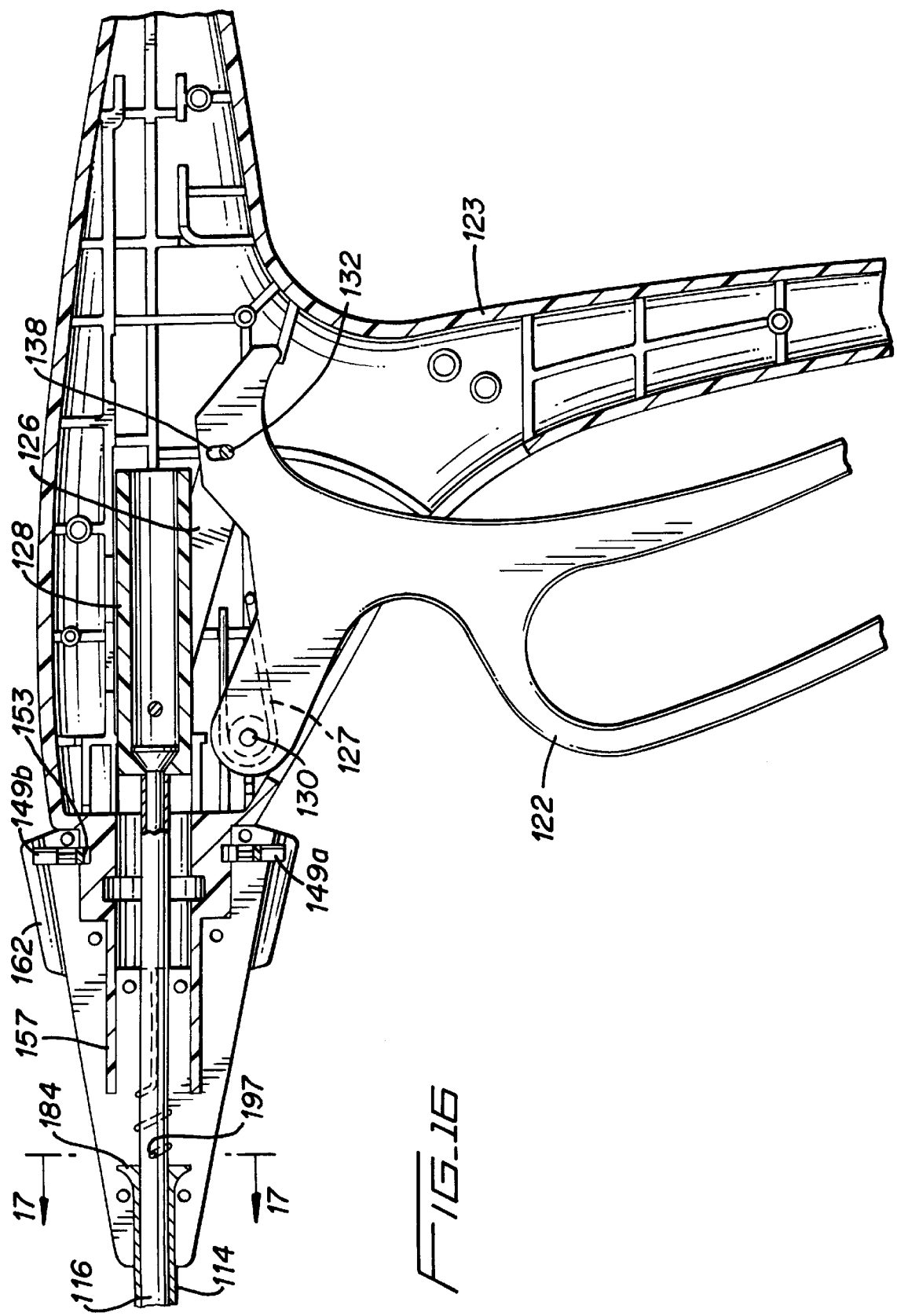

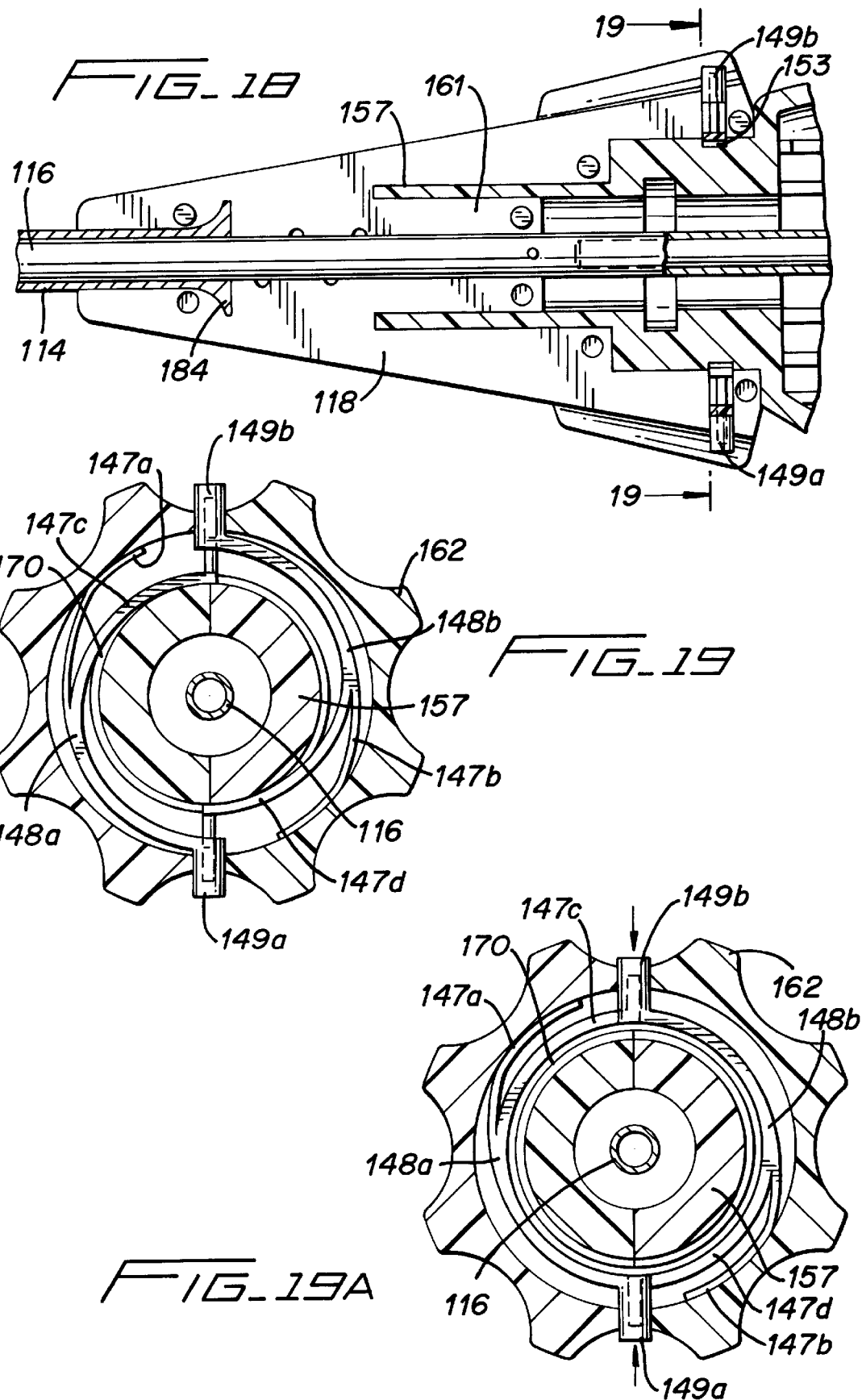

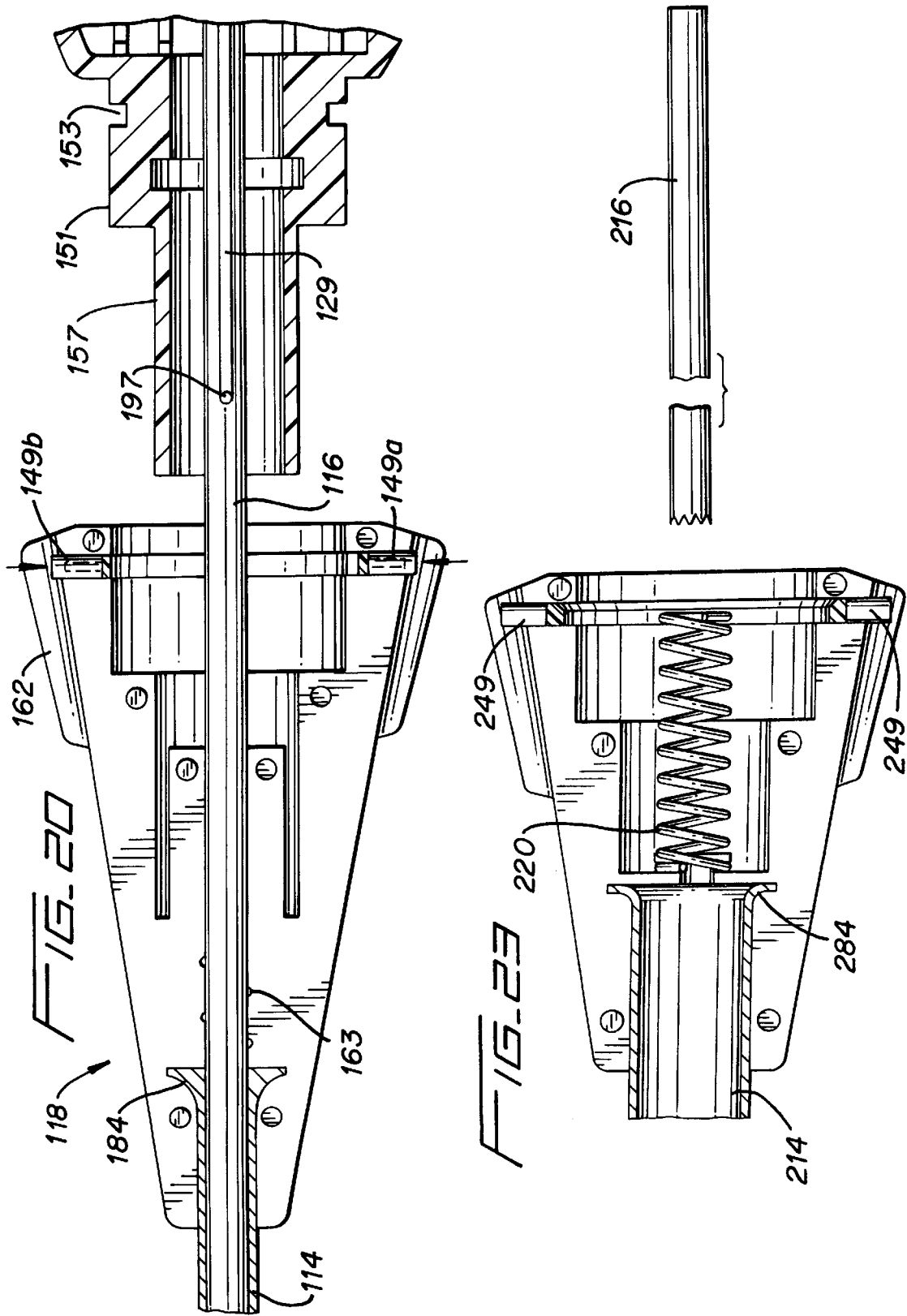

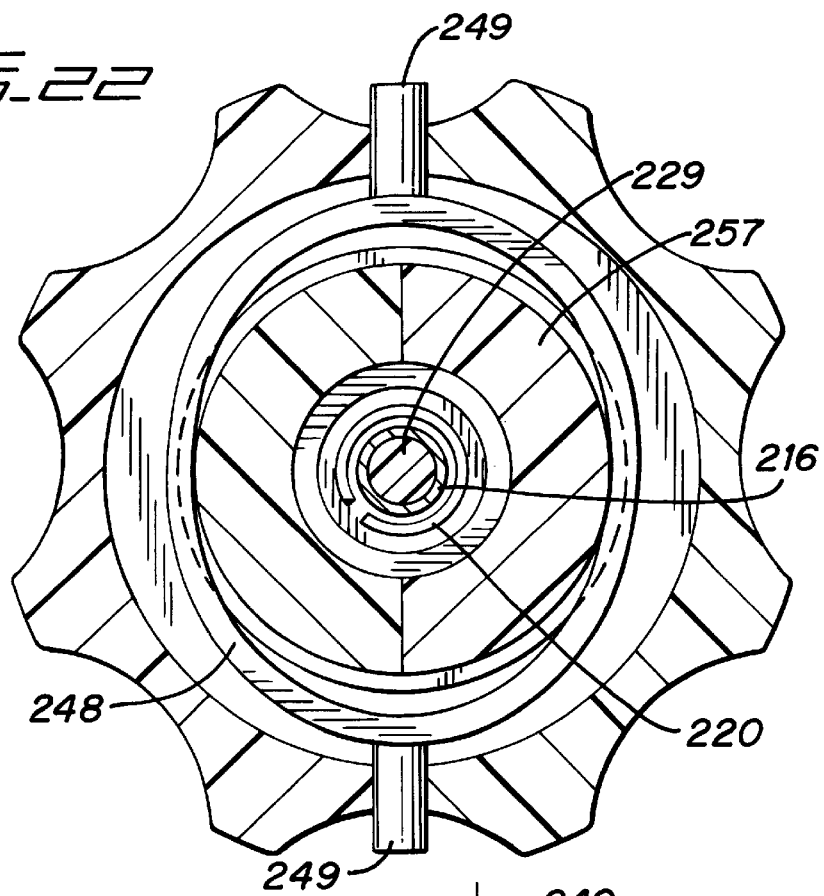
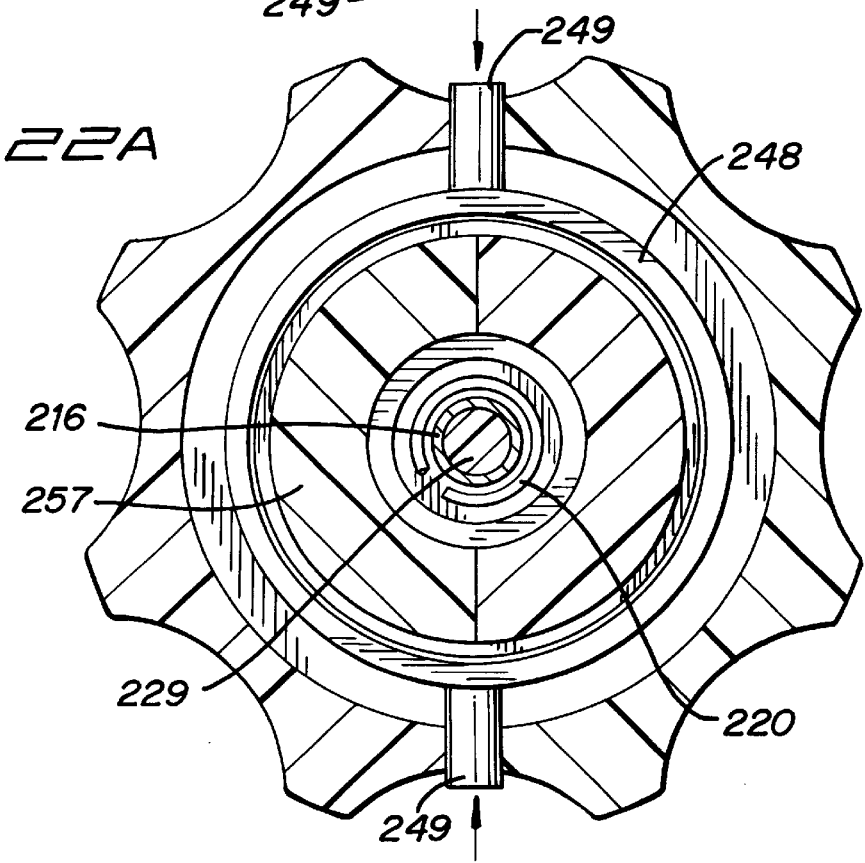

SURGICAL CUTTING APPARATUS

This is a continuation of application Ser. No. 08/416,268 filed on Apr. 4, 1995 now abandoned.

BACKGROUND

1. Technical Field

This application relates to a surgical cutting instrument, and more particularly to a surgical cutting instrument having a chamber for storing the cut tissue portions.

2. Background of Related Art

Surgical instruments for cutting body tissue are well known. One type of instrument has a pair of scissors type jaws in which either both jaws move or one jaw moves relative to the other fixed jaw in a scissors like fashion, i.e. at an angle to the longitudinal axis of the instrument. An example of this scissors type instrument is disclosed in U.S. Pat. No. 4,994,024 to Falk. Another type of cutting instrument, especially useful in orthopedic procedures for cutting hard tissue or bone, has a cutting blade which is slidable longitudinally in either a distal or proximal direction to sever the body portion. Examples of this type of instrument are disclosed in U.S. Pat. No. 5,106,364 to Hayafuji et al., U.S. Pat. No. 4,850,354 to McGurk-Burleson et al., U.S. Pat. No. 5,226,910 to Kajiyama et al., and U.S. Pat. No. 4,282,884 to Boebel.

It is also recognized that as these cutting instruments dissect the body tissue, it is advantageous to remove the tissue portions as they are dissected or to store the dissected tissue portions in the instrument. This is especially the case in endoscopic surgical procedures. Endoscopic (minimally invasive) surgical procedures are performed under visualization through either small access ports or directly through small incisions in the body. Therefore, if the dissected body tissue is not removed as it is dissected, the instrument needs to be withdrawn from the surgical site each time a tissue portion is cut, the tissue portion needs to be manually removed from the instrument, and then the instrument needs to be reinserted to the surgical site. These steps need to be repeated until the entire tissue section is removed. This repeated re-insertion of the instrument can be very time consuming, and therefore more expensive, especially in endoscopic procedures, because the surgery is being performed at a remote surgical site. The repeated insertion can also cause complications in endoscopic procedures where access to the surgical site is difficult such as in endoscopic discectomy.

As noted above, the advantages attendant removing or storing the dissected body tissue portions are well known. One way of continuously removing the tissue portion as it is dissected is by utilizing suction. One example of the use of suction is disclosed in U.S. Pat. No. 4,589,414 to Yoshida et ai. In Yoshida, a cutting member slides longitudinally in a distal direction to cut body tissue positioned in the opening in the instrument and the cut tissue is withdrawn through a suction channel in the inner tube. U.S. Pat. No. 5,007,917 to Evans discloses a rotatable cutting blade for cutting tissue and a suction tube for removing the tissue. The aforementioned patent to Falk discloses a vacuum extraction channel for use with a scissors type cutting instrument.

U.S. Pat. No. 4,282,884 to Boebel, identified above, has a storage chamber for the cut tissue. The punch assembly is slid in a proximal direction, and the punched out tissue portion is pressed into a tubular receiver member and stored therein. At the end of the procedure, the tissue portions can be removed from the receiver member.

The need exists for an improved cutting instrument for storing dissected tissue portions for removal at the end of the procedure. Such instrument would advantageously be configured to force the tissue sections into the storage chamber to prevent clogging and allow for maximum use of the space in the chamber.

SUMMARY

A surgical apparatus for cutting and storing sections of body tissue is provided comprising a housing having a handle assembly, an elongated outer tube extending from the handle assembly, and a cutting tube positioned within the outer tube and movable in response to actuation of the handle assembly between a retracted position and a distal position to cut body tissue. The cutting tube has a chamber formed therein for storing the cut tissue sections. An anvil is positioned at a distal end of the outer tube for forcing each cut tissue section proximally into the chamber of the cutting tube as the cutting tube is advanced to cut the body tissue. The cutting tube preferably has a plurality of teeth at the distal end. The outer tube preferably has a window at a distal end to receive the body tissue and the anvil is positioned distally of the window. The anvil preferably includes an enlarged head portion and a cylindrical portion of reduced diameter. The cylindrical portion enters an axial bore in the cutting tube as the cutting tube slides to its distalmost position, thereby forcing the tissue sections proximally within the cutting tube.

In one embodiment, the outer tube is connected to a tube support which is removably connected to a rotatable collar. The cutting tube is removably mounted in the outer tube. A C-clip is positioned in the collar which frictionally and releasably connects the tube support.

In an alternate embodiment, the cutting tube rotates as it is advanced distally. In this embodiment, a drive pin, connected to the cutting tube, rides in a helical groove formed in the collar during advancement of the cutting tube to effect rotation. A pair of flexible clasping members releasably mount the collar to the housing such that movement of the clasping members from a first position to a second position releases the collar from the housing. Removal of the collar likewise separates both the outer tube and the cutting tube from the housing. The cutting tube can then be removed from the outer tube to access/remove the cut tissue portions stored therein.

BRIEF DESCRIPTION OF THE DRAWINGS

Various embodiments are described herein with reference to the drawings, wherein:

FIG. 1 is a perspective view showing the surgical cutting apparatus;

FIG. 1A is an enlarged view of the distal end of the apparatus showing the cutting tube in the proximal (retracted) position;

FIG. 2 is an exploded perspective view of the apparatus of FIG. 1;

FIG. 3 is a cross-sectional view taken along lines 3—3 of FIG. 1 showing the cutting tube in the retracted position;

FIG. 3A is a cross-sectional view taken along lines 3a—3a of FIG. 3;

FIG. 4 is a cross-sectional view taken along lines 4—4 of FIG. 1 showing the pivotal handle in the initial position corresponding to the retracted position of the cutting tube;

FIG. 5 is a cross-sectional view similar to FIG. 3 showing the cutting tube in the advanced (distal) position with the anvil positioned inside to force the cut tissue section proximally;

FIG. 5A is a cross-sectional view taken along lines 5A—5A of FIG. 5;

FIG. 6 is a cross-sectional view similar to FIG. 4 showing the handle actuated to advance the cutting tube to the distal position;

FIG. 7 is an enlarged cross-sectional view showing the engagement of the tube support and the housing;

FIG. 7A is an enlarged cross-sectional view showing the disassembly of the tube support and outer tube from the housing;

FIG. 8 is a side view in partial cross-section illustrating a series of tissue sections positioned inside the cutting tube;

FIG. 8A is a cross-sectional view illustrating removal of the cutting tube from the outer tube;

FIG. 9 is a perspective view of the proximal portion of an alternate embodiment of the surgical cutting apparatus;

FIG. 10 is an exploded perspective view of the apparatus of FIG. 9;

FIG. 11 is an enlarged partially exploded perspective view showing the cutting tube and one of the collar halves;

FIG. 12 is a cross-sectional view taken along lines 12—12 of FIG. 9 illustrating the pivoting handle in the initial position corresponding to the retracted position of the cutting tube;

FIG. 12A is a cross-sectional view showing the cutting tube in the retracted position;

FIG. 13 is a cross-sectional view taken along lines 13—13 of FIG. 12;

FIG. 14 is a view similar to FIG. 12 showing the handle in the intermediate position to partially advance the cutting tube;

FIG. 14A is a view similar to FIG. 12A showing partial advancement of the cutting tube;

FIG. 15 is a cross-sectional view taken along lines 15—15 of FIG. 14;

FIG. 15A is a cross-sectional view taken through the collar showing initial rotation of the cutting tube as it is advanced distally;

FIG. 15B is a view similar to FIG. 14A showing further advancement of the cutting tube with the V-notch shown in phantom to illustrate the rotation of the cutting tube;

FIG. 16 is a cross-sectional view similar to FIG. 14 showing complete actuation of the pivoting handle to advance the cutting tube to the distal position;

FIG. 17 is a cross-sectional view taken along lines 17—17 of FIG. 16;

FIG. 17A is a cross-sectional view similar to FIG. 15B showing the cutting tube in the advanced position with the anvil positioned inside to force the cut tissue section proximally;

FIG. 18 is an enlarged view in partial cross section illustrating the engagement of the collar and the housing;

FIG. 19 is a cross-sectional view taken along lines 19—19 of FIG. 18 illustrating the pair of C-clips in the engaging position to connect the collar and the housing;

FIG. 19A is a view similar to FIG. 19 except showing movement of the C-clips to the release position to release the collar from the housing;

FIG. 20 is a cross-sectional view illustrating removal of the collar from the housing;

FIG. 22 is a cross-sectional view taken along lines 22—22 of FIG. 21 illustrating the clasping member in the engaging position to connect the collar and the housing;

FIG. 22A is a view similar to FIG. 22 except showing movement of the clasping member to the release position to release the collar from the housing; and FIG. 23 is a side view in partial cross section showing removal of the cutting tube from the outer tube.

DETAILED DESCRIPTION OF PREFERRED EMBODIMENTS

Figure 21:
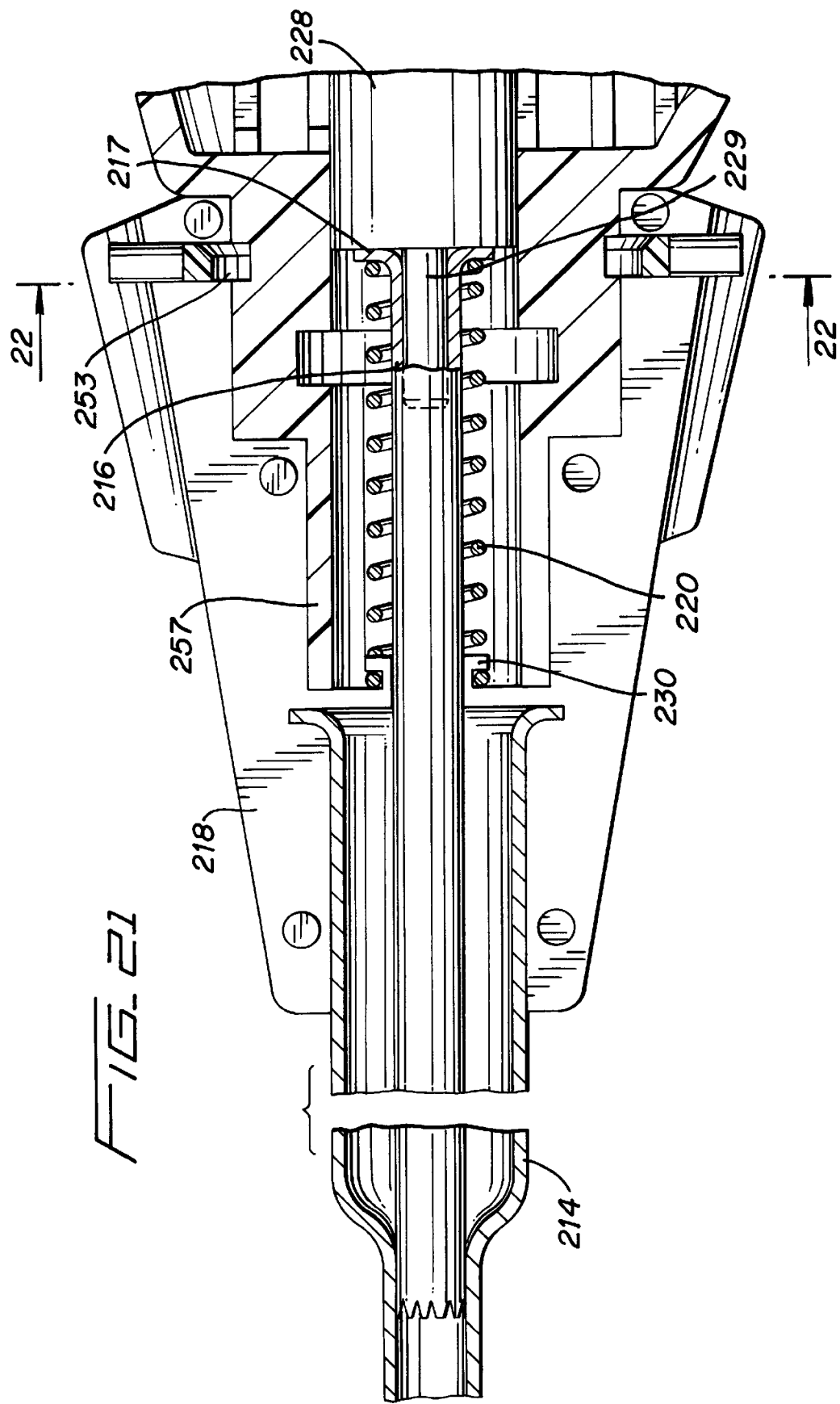
FIG. 21 is a cross-sectional view illustrating the engagement of the collar assembly and housing of an another alternate embodiment.

Referring now to the drawings and in particular to FIGS. 1 and 1A, the surgical apparatus of the first embodiment, designated generally by reference numeral 10, is illustrated for cutting body tissue. The apparatus has an elongated outer tube or body portion 14 which is dimensioned and configured for either insertion through a trocar cannula or through a small incision in the body tissue. Slidably positioned within outer tube 14 is an elongated hollow inner cutting tube 16. Cutting tube 16 is advanced distally upon actuation of handle assembly 13 to cut body tissue positioned in window 82 of outer tube 14. An anvil 92, positioned at a distal end of the outer tube 14, forces the severed body tissue portion rearwardly inside the cutting tube 16. In this manner, the apparatus can be inserted inside the body and the cutting tube 16 repeatedly advanced to cut body tissue with the anvil 92 forcing the cut tissue sections proximally in the cutting tube to allow a plurality of tissue portions to be stored therein.

The apparatus 10 can be easily disassembled to access and remove the individual tissue sections stored within the cutting tube 16. This also facilitates re-sterilization of the instrument parts for subsequent reassembly and reuse if the instrument is composed of reusable materials.

Turning now to the individual components of the apparatus 10, and first to the housing 12 as illustrated in FIGS. 1 and 2, housing 12 includes a handle assembly 13 and a collar assembly 66. Handle assembly 13 is composed of two housing halves 20a, 20b welded together and aligned via alignment pins 25. Handle 22 is pivotably mounted to housing halves 20a, 20b via mounting pin 30 extending through opening 36 such that movement of pivotal handle 22 towards stationary grip 23 drives the cutting tube 16 distally in the manner described below.

Reciprocating block 28 has a mounting pin 29 which is seated within a proximal end 91 of cutting tube 14. A pair of links 24, 26 connect handle 22 to block 28. More specifically, transverse pin 32 extends through aperture 37 in handle 22 and through slots 38, 40 in links 24, 26, respectively, to connect the links to the pivotable handle 22. Transverse pin 34 extends through aperture 46 in block 28 and through apertures 42, 44 in links 24, 26 respectively, to connect the links to block 28. Consequently, when handle 22 is moved from the position of FIG. 4 to the position of FIG. 6, block 28 is forced distally by links 24, 26 to advance cutting tube 16 mounted thereon. Spring 31 biases handle 22 to the open position.

A C-clip 48 is received within circumferential groove 50 formed in inner wall 27 of the nose portion 23 of housing 20. C-clip 48 frictionally mounts support tube 68 in the manner described below.

Rotating collar 66 has a tube support 68 positioned within a central bore 60 formed therein. Grip portion 62 of rotating collar 66 has a series of indentations 64 configured to receive the user's fingers to facilitate rotation. O-ring 49, best seen in FIGS. 2 and 4, is seated within a circumferential groove 39 formed in the outer surface of nose 23 of housing 12.

With continued reference to FIGS. 2 and 4, tube support 68 has a circumferential chamfered engaging groove 70 on the cyndrical portion 72 for receiving C-clip 48. The stepped configuration conforms to the inner surface configuration of collar 66. Passageway 74 of tube support 68 is dimensioned and configured to frictionally mount outer tube 14 such that rotation of collar 66 rotates tube support 68 and outer tube 14.

With reference to FIGS. 1A, 2 and 3, outer tube 14 of apparatus 10 has a closed distal end 80, a window 82 to receive the body tissue to be cut, and a proximal end 84 which is secured within tube support 68. Bore 85 is dimensioned to slidably receive cutting tube 16. An anvil or tissue engaging member 92 is positioned at distal end 80 of outer tube 14, with the enlarged head portion 91 fixedly attached thereto. Reduced diameter cyndrical portion 97, terminates in contact surface 93 and is configured to force tissue proximally within cutting tube 16.

Cutting tube 16, as shown in FIGS. 2 and 4, has a proximal end 91 which is fitted over mounting pin 29 of block 28 as discussed above. A V-shaped notch 94 is stamped in distal end 90 of cutting tube 14 and forms a gripping surface 96 (see FIG. 3A) to help retain tissue. A plurality of cutting teeth 98 are formed at the distalmost end to cut the body tissue positioned in window 82 of outer tube 14 as the cutting tube 16 is advanced distally. The cutting tube 16 has an axial bore 95 which forms a chamber for storing the individual tissue portions as they are cut. Anvil 92 forces the cut tissue section rearwardly into axial bore or chamber 95 to create space in the cutting tube 16 for receiving the next tissue section when cutting tube 16 is once again advanced to cut tissue.

As noted above, C-clip 48 frictionally and releasably retains tube support 68 within nose 23 of housing 20. Consequently, at the end of the procedure, outer tube 14 or tube support 68 can be grasped by the user and pulled distally to disengage tube support 68 from C-clip 48 as shown in FIG. 7A. After the tube support 68 and outer tube 14 are removed from the housing 20, the cutting tube 16 is pulled proximally through the opening 87 in proximal end 84 of outer tube 14. The tissue sections can then be removed and organized for pathology.

The disassembly also facilitates re-sterilization of the apparatus if it is intended for reuse. However, it should be appreciated, that alternatively the apparatus can be entirely disposable and can be discarded after use. It can also be partially disposable with some parts discarded e.g. the tube support and tubes, and the remaining parts, e.g. the handle assembly, reused.

In use, with reference initially to FIGS. 3, 3A and 4, pivoting handle 22 is spaced from grip portion 23 and reciprocating block 28 is in the proximalmost position thereby maintaining cutting tube 16 in the proximal (retracted) position.

The apparatus is inserted into the body, either through a cannula or directly through a small incision, and the outer tube 14 is placed adjacent the surgical site such that the tissue to be severed is seated within window 82. Handle 22 is actuated by squeezing it towards grip portion 23 to move block 28 distally to advance cutting tube 16 distally towards anvil 92 as shown in FIGS. 6, 5 and 5A. The teeth 98 of the cutting tube 16 pass through the window 82 to pierce and dissect the body tissue seated therein. As the cutting tube 16 passes over cylindrical portion 97 of anvil 92 such that cylindrical portion 97 enters the hollow interior of the cutting tube 16, contact surface 93 of anvil 92 forces the dissected tissue proximally into the cutting tube 16. Enlarged head 91 acts as a positive stop for cutting tube 16. After dissection, handle 22 is released, returning cutting blade 16 to the proximal position of FIG. 4.

The user can then once again squeeze handle 22 to advance cutting blade 16 to dissect another portion of the body tissue positioned in window 82. As the cutting tube 16 advances to its distalmost position, contact surface 93 of anvil 92 once again forces the dissected tissue rearwardly (proximally) into cutting tube 16. The cutting tube 16 can be repeatedly advanced and retracted in this manner to dissect the entire desired portion of body tissue, with the anvil 92 advantageously forcing the body tissue sections proximally to provide room for the next body tissue portion. FIG. 8A illustrates a plurality of body tissue sections T positioned within cutting tube 16.

After use, to disassemble the instrument to remove the tissue from the cutting tube 16, outer tube 14 or tube support 68 is pulled in a distal direction (see arrow A of FIG. 7A), overcoming the clasping force of C-clip 48.

After the support tube 68 and the mounted outer tube 14 (and cutting tube 16) have been removed as shown in FIG. 8, cutting tube 16 is pulled proximally (arrow B) out of the proximal opening 81 in outer tube 14 and proximal opening 87 in tube support 68 as shown in FIG. 8A. The tissue sections T can then be removed from cutting tube 16 and arranged in a manner similar to their configuration prior to dissection to assist in examination and testing of the tissue.

To reassemble the instrument for subsequent use, cutting tube 16 is inserted through tube support 68 into outer tube 14 and the assembly is forced into collar 66 so that the C-clip 48 will re-engage groove 70 of tube support 68.

An alternate embodiment of the apparatus is illustrated in FIGS. 9–21. The apparatus of FIG. 9, is substantially identical to the apparatus of the first embodiment (FIGS. 1–8) except for the collar and the movement of the cutting tube.

The apparatus of this alternate embodiment, designated generally by reference numeral 100, as shown in FIG. 9, has a housing 112 having a handle assembly 113 and a collar 118. An elongated shaft or outer tube 114 extends from the tapered nose portion 155 of the collar 118. As in the first embodiment, a handle 122 is pivotably mounted with respect to grip portion 123 for moving cutting tube 116 between its proximal (retracted) position and its distal (advanced) cutting position.

With reference to FIG. 10, the linkage mechanism of this embodiment is identical to that of the embodiment of FIG. 1 except for the mounting pin 129. That is, transverse pin 130 connects pivotal handle 122 to housing halves 120a, 120b; transverse pin 132 extends through slots 138 and 140 of links 124, 126 to connect the links to the handle 122 through aperture 137; and transverse pin 134 extends through apertures 142, 144 of link 124, 126 and opening 146 in reciprocating block 128, to mount the links to the block. Alignment pins 125 align housing halves 120a, 120b. Mounting pin 129 extends through bore 131 in block 128 and has an aperture 133 for receiving drive pin 197 (described below) to connect mounting pin 129 to the proximal end of cutting tube 116.

The nose portion 157 of the housing 120 includes an axial bore 152 configured to receive section 161 of collar 118. An outer circumferential groove 153 is formed in wall 151 of nose portion 157 to receive a pair of mounting clips 148a, 148b for detachably mounting the collar 118 in the manner described below.

The collar 118, as best shown in FIGS. 10 and 11, is composed of two collar halves 118a, 118b which are identical in configuration. Collar 118 has a central bore 160 dimensioned to receive outer tube 114. Helical groove 163 is formed within collar 118 to provide longitudinal and rotational motion of the cutting tube 116 as it advances distally. The linear groove portion 165 provides initial longitudinal translation of the cutting tube 116 without rotational movement in the manner described below.

Mounting pins 167b, 167c, 167d and 167e of collar half 118b are received in corresponding apertures in collar half 118a. Similarly, four mounting pins (not shown) projecting from collar half 118a extend into apertures 167f, 167g, 167h and 167i formed in collar half 118b.

Referring back to FIG. 10, the pair of flexible C-clips 148a, 148b are each mounted in a respective semi-circular groove 170 formed on the inner surface of collar halves 118a, 118b. C-clip 148b has a leaf spring portion 147b and a projection 149b slidably positioned within slot 171 of collar half 118b. Similarly, C-clip 148a has a leaf spring portion 147a and a projection 149a slidably received within slot 171 in collar half 118a. Engaging portions 147c, 147d of C-clips 148a, 148b, respectively, are seated in a portion of outer circumferential groove 153 of nose 157 for detachably mounting collar 118.

Grip portion 162 is positioned at the proximal end of the collar 118 and includes indentations 164 configured to receive the user's fingers to facilitate rotation. Outer shaft 114 is fixed within central bore 160 of collar 118 such that rotation of collar 118 rotates outer tube 114 (and cutting tube 116 positioned therein).

Inner cutting tube 116, as shown in FIGS. 10 and 11, has a transversely extending drive pin 197 extending therefrom which travels within linear groove portion 165 and helical groove portion 163 of the collar 118. In all other respects, the cutting tube 116 is identical to the cutting tube 16 of the embodiment of FIG. 1 as it includes a V-notch 194, a plurality of cutting teeth 198, and an axial bore or chamber 199 for storing the cut tissue sections.

The outer tube 114 is identical in configuration to the outer tube 14 of FIG. 1 except that it is mounted at a proximal end to the collar 118 as shown in FIGS. 11 and 12 and has a flared portion 184 at its proximal end for mounting to collar 118. Outer tube 114 includes a central bore 185 and a window 182 dimensioned for receiving tissue at the distal end portion 186. Anvil 192, identical in configuration and function to anvil 92 of the embodiment of FIG. 1, is fixedly mounted at distal end portion 186 of outer tube 114 and has a tissue contacting surface 193.

In use, in the initial position of FIGS. 12 and 12A, pivoting handle 122 is biased away from grip portion 123 by spring 127 and cutting tube 116 is in the proximalmost (retracted) position. In this position, the drive pin 197 is in the proximalmost portion of linear groove portion 165 of collar 118.

To advance the cutting tube 116, handle 122 is actuated by moving it towards stationary grip 123, as shown in FIG. 14, causing links 124, 126 to drive reciprocating block 128 distally, thereby forcing cutting tube 116 distally. As shown in FIG. 14A, during this initial advancement, cutting tube 116 is advanced longitudinally into the window 182 towards anvil 192 without rotational motion. Note that in this intermediate position of cutting tube 116, drive pin 197 is positioned in the distalmost portion of linear groove portion 165.

As pivotal handle 122 is moved to its fully squeezed (actuated) position as shown in FIG. 16, the cutting tube 116 is advanced from the position shown in FIG. 14A to its distal position shown in FIG. 17A. During this stage of advancement, drive pin 197 travels in the helical groove portion 163 of collar 118, thereby causing rotational movement of the cutting tube 116 along with longitudinal movement, as best seen by comparing FIGS. 15 and 15A, and FIGS. 15B and 17A. This rotational motion facilitates cutting of the tissue positioned in the window 182. Note that the V-shaped notch is shown in phantom in FIG. 15B for the convenience of the reader to illustrate the rotational motion of the cutting tube 116. The anvil 192 forces each dissected tissue section proximally into axial bore 199 of cutting tube 116 in the same manner as described above.

As in the embodiment of FIGS. 1–8, the second embodiment of FIGS. 9–20 can also be readily disassembled to remove the tissue sections stored in cutting tube 116. However, in the embodiment of FIGS. 9–20, the collar 118 is detached from the handle assembly 113 along with the outer tube 114 and cutting tube 116. As best shown in FIG. 18 and 19, in the initial position, projections 149a, 149b of C-clips 148a, 148b extend through slots 171 in the collar halves 118a, 118b, respectively, and the engaging portions 147c and 147d engage a portion of circumferential groove 153 of nose portion 157 of housing 120.

To detach the collar 118, projections 149a, 149b of the respective C-clips are forced radially inwardly in the direction of the arrows of FIG. 19a against the biasing force of leaf spring portions 147a, 147b. This causes the C-clips to bow radially outwardly into a circular configuration such that engaging portions 147c, 147d disengage circumferential groove 153. Consequently, collar 118 is released and can be pulled distally to separate from nose portion 157 (FIG. 20). Pin 197 can then be removed to separate cutting tube 116 from the mounting pin 129. The tissue sections can then be removed and analyzed as described above with respect to the embodiment of FIG. 1.

To reassemble the instrument for subsequent use if desired, cutting tube 116 is re-attached to mounting pin 129 via drive pin 197 and outer tube 114 is slid over cutting tube 116 as the collar 118 is slid over nose portion 157. C-clips 148a, 148b, normally biased to the engaging position, will re-engage the circumferential groove 153 to secure collar 118 to the housing 20.

Another alternate embodiment of the apparatus is illustrated in FIGS. 21–23. In this embodiment, the cutting tube 216 has a flared portion 217 and a spring 220 is positioned between the flared portion 217 and wall 230 of collar 218 to bias the cutting tube 216 proximally. The proximal end portion of cutting tube 216 is seated over pin 229 which extends through block 228. Outer tube 214 tapers at its distal end to improve access to the surgical site. Preferably the outer tube 214 has an outer diameter of approximately 10 mm which tapers to an outer diameter of 5 mm, although other dimensions are also contemplated. Note in all other respects, cutting tube 216 and outer tube 214 are identical to cutting tube 116 and outer tube 114 of the embodiment of FIG. 9.

Instead of the pair of C-clips of FIGS. 9–20, a one piece flexible circular clasp 248 is provided (FIGS. 22, 22A) to releasably mount the collar 218 to the nose portion 257 of the housing. In a similar fashion to the C-clips 148a, 148b described above, circular clasp 248 assumes a non-circular shape as shown in FIG. 22 when in the clasping position to mount collar 218 to the nose portion 257. In this clasping position, a portion of clasp 248 is seated within circumferential groove 253 of nose portion 257. When it is desired to detach collar 218 from the housing, projections 249 are pressed inwardly as shown in FIG. 22A, forming flexible clasp 248 into a circular shape for release from circumferential groove 253 of nose portion 257. This enables the collar 218 to be separated from nose portion 257.

In this embodiment, to disassemble the instrument, after collar 218 is removed from the nose portion in the manner described above, cutting tube 216 is pulled proximally out of opening 284 in outer tube 214 (FIG. 23). The tissue sections contained in the cutting tube 16 can then be removed. As can be appreciated, in this embodiment, the removal of a separate pin (i.e. pin 197 of FIG. 20) is avoided. Note that the housing and handle portions are identical to that of FIGS. 9–20 in all other respects and are therefore not illustrated or further described herein.

The instruments 10 and 100 can be used to dissect tissue in a variety of surgical procedures. For example, in endoscopic discectomy procedures, the instrument can be inserted into the disc space to quickly dissect portions of the disc. The cutting tube can then be removed in the manner described above and the tissue sections removed and analyzed. The instrument can also be used as a ronguer for cutting and storing sections of bones in other surgical procedures.

It will be understood that various modifications may be made to the embodiments disclosed therein. For example, a cutting tube having different teeth configurations or having other cutting configurations such as a beveled edge can be utilized. Moreover, the instrument can be either disposable or reusable. Therefore, the above described should not be construed as limiting, but merely as exemplifications of preferred embodiments. Those skilled in the art will envision other modifications within the scope and spirit of the claims appended hereto.

What is claimed is:

1. A surgical apparatus for cutting and storing sections of body tissue comprising:
   a housing having a handle assembly;
   an elongated outer tube extending from the handle assembly and having an opening in an outer wall portion thereof defining a window for reception of body tissue;
   a cutting tube positioned within the outer tube and movable in response to activation of the handle assembly between a proximal position and a distal position to sever body tissue, the cutting tube having a chamber formed therein for storing tissue sections severed thereby and defining a distal cutting end the distal cutting end being open,
   a rotatable collar operatively associated with the outer tube and rotatably mounted to the housing, the rotatable collar rotatable to cause corresponding rotational movement of the outer tube to thereby selectively position the window at predetermined angular positions for reception of the body tissue; and
   an anvil positioned at a distal end portion of the outer tube and disposed adjacent to the window, the anvil dimensioned to be at least partially received within the distal cutting end of the cutting tube when the cutting tube is in the distal position thereof wherein the body tissue received within the window of the outer tube is supported by the anvil and at least severed through the cooperative interaction of the distal cutting end of the cutting tube and the anvil, the anvil further configured for engaging and forcing severed tissue sections proximally into the chamber of the cutting tube during movement of the cutting tube.

2. The apparatus of claim 1, wherein the outer tube and cutting tube are removably connected to the housing.

3. The apparatus of claim 2, wherein the cutting tube is removably mounted in the outer tube.

4. The apparatus of claim 1, wherein the rotatable collar is mounted to the housing and the outer tube and the cutting tube are detachably mounted to the rotatable collar.

5. The apparatus of claim 4, further comprising a tube support mounted within the collar and having a central bore for receiving the outer tube and a circumferential groove for receiving a C-clip, the C-clip frictionally and releasably connecting the tube support to the collar.

6. The apparatus of claim 1, wherein the distal cutting end of the cutting tube includes a plurality of teeth.

7. The apparatus of claim 1, wherein the cutting tube includes a notch adjacent the distal end to facilitate retention of tissue in the chamber formed therein.

8. The apparatus of claim 1, wherein the anvil is positioned distally of the window in the outer tube.

9. The apparatus of claim 8, wherein the anvil includes an enlarged head portion and a cylindrical portion of reduced diameter, the cylindrical portion entering an axial bore formed in the cutting tube upon movement of the cutting tube to the distal position to thereby force the severed tissue sections proximally within the cutting tube.

10. The apparatus of claim 1, wherein the cutting tube rotates as it is advanced distally.

11. The apparatus of claim 10, further comprising a helical groove formed in the rotatable collar and a drive pin extending from the cutting tube, wherein the drive pin rides in the helical groove during advancement of the cutting tube to effect rotation of the cutting tube.

12. The apparatus of claim 11, wherein the distal cutting end of the cutting tube has a plurality of teeth.

13. A surgical apparatus for cutting and storing tissue comprising:
   a housing including a handle assembly and a mounting collar, the mounting collar having structure for releasable attachment to the handle assembly;
   an elongated body portion extending from the housing and connected to the mounting collar, such that removal of the mounting collar from the housing removes the elongated body portion;
   a cutting tube slidably positioned within the elongated body portion for movement upon actuation of the handle assembly from a proximal position to a distal position to cut body tissue, the cutting tube having an open distal end; and
   a tissue engaging member fixedly positioned at a distal end portion of the elongated body portion, the tissue engaging member having an engaging surface, the engaging surface being received within the open distal end of the cutting tube when the cutting tube in the distal position thereof to at least support the body tissue to facilitate cutting there of by the cutting tube, and being configured for engaging and forcing body tissue sections cut by the cutting tube proximally through the open distal end and within the cutting tube.

14. The apparatus of claim 13, further comprising a flexible clasping member for releasably mounting the mounting collar to the housing, wherein movement of the clasping member from a first position to a second position releases the mounting collar from the housing.

15. The apparatus of claim 14, wherein removal of the collar from the housing removes the elongated body portion and the cutting tube.

16. The apparatus of claim 15, wherein the cutting tube is removably mounted in the elongated body portion to allow release thereof when the elongated body portion is disengaged from the housing.

17. The apparatus of claim 16, wherein the body portion has an opening at a proximal end to allow removal of the cutting tube.

18. The apparatus of claim 14, wherein the clasping member includes at least one projection extending though an opening in the collar assembly.

19. A surgical apparatus for cutting and storing sections of body tissue, which comprises:

a handle including a pistol grip having a depending stationary grip portion and a depending movable grip portion;

an endoscopic portion including:

an elongated outer tube extending from the handle and having an opening defined in an outer wall portion thereof defining a window for reception of tissue;

a cutting tube disposed within the outer tube and operatively connected to the movable grip portion, the cutting tube distally advanceable to a cutting position thereof in response to movement of the movable grip portion and having a distal cutting edge to sever tissue received within the window of the outer tube, the cutting tube having a longitudinal bore defining a chamber therein for accommodating severed tissue sections; and a tissue engaging member disposed at a distal end portion of the outer tube adjacent the window, the tissue engaging member defining an inner tissue engaging surface dimensioned and configured to e at least partially received within the internal chamber upon movement of the cutting tube to cutting position thereof and to thereby support the tissue received within the window to facilitate severing thereof and to subsequently engage and force the severed tissue sections proximally within the chamber; and a rotatable collar operatively associated with the cutting tube and rotatably mounted to the housing, the rotatable collar rotatable to cause corresponding rotational movement of the cutting tube to thereby selectively position the window at predetermined angular positions for reception of the body tissue.

20. The surgical apparatus according to claim 19 wherein the opening in the outer wall portion is defined by a blunt edge.

21. A surgical apparatus for cutting and storing tissues which comprises:

a housing having an actuating member;

an elongated outer tube extending from the housing and having an opening in an outer wall portion thereof defining a window for reception of body tissue;

a cutting tube positioned within the outer tube and movable in response to actuation of the actuating member between a proximal position and a distal position to sever body tissue, the cutting tube having an inner chamber for storing tissue sections severed thereby;

a rotatable collar rotatablvy mounted to the housing and defining a longitudinal bore for receiving at least a portion of the cutting tube;

a clasping member mounted to the rotatable collar and operatively engageable with the outer tube, the clasping member moveable between an engaged position wherein the rotatable collar and the outer tube are in operative engagement such that rotational movement of the rotatable collar causes corresponding rotational movement of the outer tube to thereby selectively position the window of the outer tube at predetermined angular orientations, and a disengaged position wherein the clasping member is operatively disengaged from the outer tube to permit the outer tube to be disassembled from the rotatable collar; and a manually engagable member associated with the clasping member and extending beyond the rotatable collar, to be accessed by a user, the manually engagable member movable to at least move the clasping member to the disengaged position thereof.

\* \* \* \* \*